United States Patent
Lewis et al.

(10) Patent No.: US 8,456,633 B2
(45) Date of Patent: *Jun. 4, 2013

(54) SPECTROMETRIC PROCESS MONITORING

(75) Inventors: E. Neil Lewis, Brookeville, MD (US);
Kenneth S. Haber, Frederick, MD (US)

(73) Assignee: Malvern Instruments Incorporated, Westborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/387,643

(22) Filed: May 5, 2009

(65) Prior Publication Data

US 2010/0097599 A1    Apr. 22, 2010

Related U.S. Application Data

(63) Continuation of application No. 10/328,713, filed on Dec. 23, 2002, now Pat. No. 7,528,957.

(60) Provisional application No. 60/343,449, filed on Dec. 21, 2001, provisional application No. 60/343,691, filed on Dec. 21, 2001, provisional application No. 60/394,053, filed on Jul. 3, 2002, provisional application No. 60/394,054, filed on Jul. 3, 2002.

(51) Int. Cl.
*G01N 21/25* (2006.01)

(52) U.S. Cl.
USPC .......................................... 356/419

(58) Field of Classification Search
USPC ................... 356/73, 417, 419, 337
See application file for complete search history.

(56) References Cited

U.S. PATENT DOCUMENTS

| | | | | |
|---|---|---|---|---|
| 4,054,389 A | * | 10/1977 | Owen | 356/419 |
| 5,143,224 A | * | 9/1992 | Burchell | 356/301 |
| 5,272,518 A | * | 12/1993 | Vincent | 356/419 |
| 5,440,388 A | * | 8/1995 | Erickson | 356/456 |
| 5,568,266 A | * | 10/1996 | Ciza et al. | 356/402 |
| 5,699,448 A | * | 12/1997 | Gorenflo et al. | 382/151 |
| 5,880,830 A | * | 3/1999 | Schechter | 356/318 |
| 6,104,491 A | | 8/2000 | Trainer | |
| 6,246,474 B1 | | 6/2001 | Cerni et al. | |
| 6,252,658 B1 | | 6/2001 | Togawa et al. | |
| 6,253,162 B1 | * | 6/2001 | Jarman et al. | 702/179 |
| 6,313,423 B1 | * | 11/2001 | Sommer et al. | 356/301 |
| 6,323,944 B1 | * | 11/2001 | Xiao | 356/73 |
| 6,421,121 B1 | | 7/2002 | Haavig et al. | |
| 6,690,464 B1 | * | 2/2004 | Lewis et al. | 356/326 |
| 7,295,310 B2 | | 11/2007 | Nieuwenhuis et al. | |

FOREIGN PATENT DOCUMENTS

| | | | |
|---|---|---|---|
| EP | 0980516 | * | 2/2000 |
| EP | 0980516 B1 | | 2/2000 |
| WO | WO9740360 | * | 10/1997 |
| WO | WO9740360 A1 | | 10/1997 |

* cited by examiner

Primary Examiner — Kara E Geisel
(74) Attorney, Agent, or Firm — Kristofer E. Elbing

(57) ABSTRACT

Spectrometric apparatus that include an array of detector elements and exhibits a number of capabilities is disclosed. The elements can be responsive to incident radiation to produce an output signal that includes information from the incident radiation. A spectrally selective element can be located in an optical path between the radiation source and the array, with an analysis module responsive to the output signal operative to analyze spatial distribution of spectral information received by the array. The apparatus can also correct for differences in intensity and spectral variability for spectral image signals and/or compare the spectral image signals with a pattern in spatial-spectral coordinate space. Detector elements can be responsive to scattering, and spatial information in their output can be analyzed.

94 Claims, 13 Drawing Sheets

'Concentration'

SPECTROMETRIC PROCESS MONITORING

CROSS-REFERENCE TO RELATED APPLICATION

This application is a continuation of Ser. No. 10/328,713, Dec. 23, 2002, now U.S. Pat. No. 7,528,957, which claims the benefit under 35 U.S.C. 119(e) of U.S. provisional applications entitled "ARRAY-BASED SPECTROMETRIC PROCESS MONITORING," Ser. No. 60/343,449, filed on Dec. 21, 2001; "PATTERN RECOGNITION IN HYBRID SPATIAL-SPECTRAL SPACE," Ser. No. 60/343,691, filed on Dec. 21, 2001; "SPECTROMETRIC PROCESS MONITORING," Ser. No. 60/394,053, filed on Jul. 3, 2002; and "SPECTROMETRIC PROCESS MONITORING," Ser. No. 60/394,054, filed on Jul. 3, 2002; which are all herein incorporated by reference.

FIELD OF THE INVENTION

This invention pertains to spectrometric instruments, and more particularly to array-based spectrometric instruments for process monitoring or other applications.

BACKGROUND OF THE INVENTION

Imaging spectrometers have been applied to a variety of disciplines, such as the detection of defects in industrial processes, satellite imaging, and laboratory research. These instruments detect radiation from a sample and process the resulting signal to obtain and present an image of the sample that includes spectral and chemical information about the sample. These instruments generally include some type of spectrally selective element to separate wavelengths of radiation received from the sample, and a first-stage optic, such as a lens, to focus or concentrate the radiation onto an imaging array.

SUMMARY OF THE INVENTION

Several aspects of the invention are presented in this application. These are applicable to a number of different endeavors, such as laboratory investigations, microscopic imaging, infrared, near-infrared, visible absorption, Raman and fluorescence spectroscopy and imaging, satellite imaging, quality control, industrial process monitoring, combinatorial chemistry, genomics, biological imaging, pathology, drug discovery, and pharmaceutical formulation, testing, and counterfeit detection.

In one general aspect, the invention features a spectrometric apparatus that includes an array of detector elements that are responsive to incident radiation from a radiation source to produce an output signal that includes information from the incident radiation. A spectrally selective element is located in an optical path between the radiation source and the array, and an analysis module is responsive to the output signal from the detector elements and operative to analyze spatial distribution of spectral information received by the array.

In preferred embodiments, the analysis module can be a statistical analysis module. The analysis module can be operative to compute a mean value of spectral information received by different detectors in the array. The analysis module can be operative to compute a concentration from the mean. The analysis module can be operative to compute a skew value for the spatial distribution of spectral information received by the array. The analysis module can be operative to compute a standard deviation for the spatial distribution of spectral information received by the array. The analysis module can be operative to compute a kurtosis value for the spatial distribution of spectral information received by the array. The analysis module can be operative to analyze a spatial distribution of chemical species concentration. The analysis module can be operative to analyze a spatial distribution of a plurality of chemical species concentrations. The analysis module can be operative to analyze the spatial distribution by calculating concentrations for the plurality of species at each pixel and then combining results of these concentration calculations. The array can be an array of infrared detector elements that are responsive to incident infrared radiation to produce the output signal. The array can be an array of near-infrared detector elements that are responsive to incident near-infrared radiation to produce the output signal. The array can be an array of ultraviolet detector elements that are responsive to incident ultraviolet radiation to produce the output signal. The array can be an array of visible-range detector elements that are responsive to incident visible light to produce the output signal. The source can be a narrow-band source with the array and the spectrally sensitive element being operative on wavelengths outside of the bandwidth of the source. The detector array can be a two-dimensional detector array. The analysis module can include multivariate spectral analysis logic responsive to the output signal. The analysis module can include component analysis logic. The apparatus can further include a display module responsive to the analysis module and operative to provide a display signal that expresses results from the analysis module. The apparatus can further include a threshold module responsive to the analysis module and operative to provide an accept/reject signal that expresses results from the analysis module. The analysis module can be operative to compute both an overall amount value and spatial distribution information from the output signal of the detector array.

In another general aspect, the invention features a spectrometric detection method that includes distributing a heterogeneous material including a plurality of species over an area within a field of view of a detector array, acquiring spectral image data from the material using the array, and reporting the detection of a plurality of radiation wavelengths from at least one of the species.

In preferred embodiments, the species can be each different homogeneous chemical species. The step of acquiring can take place for infrared wavelengths. The step of acquiring can take place for near-infrared wavelengths. The step of acquiring can take place for ultraviolet wavelengths. The step of acquiring can take place for visible wavelengths. The step of acquiring can take place for wavelengths outside of a bandwidth of the source. The step of acquiring can be performed by a two-dimensional detector array. The step of reporting can be responsive to a multivariate spectral analysis step.

In a further general aspect, the invention features a spectrometric apparatus that includes an array of detector elements that are responsive to incident radiation from a radiation source to produce an output signal that includes information from the incident radiation, a spectrally selective element in an optical path between the radiation source and the array, a spreading element operative to spread a sample onto a field of view of the array, and an analysis module operative to derive a spectral image data set from the sample.

In preferred embodiments, the spreading element can be a widened transparent conduit placed in a field of view of the array. The spreading element can include a flow obstacle. The array can be an array of infrared detector elements that are responsive to incident infrared radiation to produce the output signal. The array can be an array of near-infrared detector elements that are responsive to incident near-infrared radiation to produce the output signal. The array can be an array of ultraviolet detector elements that are responsive to incident ultraviolet radiation to produce the output signal. The array can be an array of visible-range detector elements that are responsive to incident visible light to produce the output signal. The source can be a narrow-band source and wherein the array and the spectrally sensitive element are operative on wavelengths outside of the bandwidth of the source. The detector array can be a two-dimensional detector array. The analysis module can include multivariate spectral analysis logic responsive to the output signal.

In another general aspect, the invention features a spectrometric apparatus that includes an integrated array of detector elements that are at least generally aligned in at least a first direction, and that are responsive to incident radiation to produce an output signal that includes information from the incident radiation, and a variable filter deposited on the surface of the integrated array and having spectral characteristics that vary along at least the first direction.

In preferred embodiments, the integrated array can be an array of infrared detector elements that are responsive to incident infrared radiation to produce the output signal. The integrated array can be an array of ultraviolet detector elements that are responsive to incident ultraviolet radiation to produce the output signal. The integrated array can be an array of visible-range detector elements that are responsive to incident visible light to produce the output signal. The apparatus can further include a narrow-band source, with the detector array and the variable filter being operative on wavelengths outside of the bandwidth of the source. The detector array can be a two-dimensional detector array. The variable filter can be a variable band-pass filter. The variable filter can be a continuously variable filter. The apparatus can further include multivariate spectral analysis logic responsive to the output signal. The apparatus can further include a plurality of separate optical channeling elements positioned in optical paths that pass through parts of the variable filter having different spectral characteristics to different detector elements. The apparatus can further include a vessel wall on which the array is mounted. The array can be a semiconductor array and the variable filter is deposited directly on the semiconductor array itself. The variable filter can be deposited on an intermediate layer. The apparatus can further include an actuator operative to move one of the filter, the array, or a sample relative to at least another of the filter, the array, or the sample. The apparatus can further include an indirect driver operative to move the sample relative to the filter and/or the array. The indirect driver can be a passive driver. The indirect driver can be incidental to a process being monitored by the array.

In a further general aspect, the invention features a spectrometric apparatus that includes an array of detector elements that are at least generally aligned in at least a first direction, and that are responsive to incident radiation to produce an output signal that includes information from the incident radiation, a variable filter having spectral characteristics that vary along at least along the first direction, at least one vessel having a volume disposed in a field of view of the array of detector elements through the variable filter, and an indirect driver operative to move contents of the vessel through the field of view of the array.

In preferred embodiments, the indirect driver can be a passive driver. The driver can be a gravity-driven flow channel. The driver can be restricted gravity-driven flow channel. The driver can operate by one of the following mechanisms: elution, sedimentation, capillary action, viscous friction, evaporation, convection, and gravity The indirect driver can be incidental to a process being monitored by the array. The driver can be a heat source. The driver can be a mixing element. The apparatus can further include an externally applied gradient driver applied perpendicularly to an axis of progression of the indirect driver. The array can be an array of infrared detector elements that are responsive to incident infrared radiation to produce the output signal. The array can be an array of ultraviolet detector elements that are responsive to incident ultraviolet radiation to produce the output signal. The array can be an array of visible-range detector elements that are responsive to incident visible light to produce the output signal. The apparatus can further include a narrow-band source and wherein the detector array and the variable filter are operative on wavelengths outside of the bandwidth of the source. The detector array can be a two-dimensional detector array. The variable filter can be a variable band-pass filter. The variable filter can be a continuously variable filter. The apparatus can further include multivariate spectral analysis logic responsive to the output signal.

In another general aspect, the invention features a spectrometric apparatus that includes an array of detector elements that are at least generally aligned in at least a first direction, and that are responsive to incident radiation to produce an output signal that includes information from the incident radiation, a variable filter having spectral characteristics that vary along at least along the first direction, and at least one vessel having a volume disposed in a field of view of the array of detector elements through the variable filter, wherein the elements of the array are each responsive a corresponding portion of the sample along substantially parallel optical paths.

In preferred embodiments, the vessel can be coupled to the array without any intermediate optical elements except the variable filter. The vessel can form part of an open process conduit.

In a further general aspect, the invention features a spectrometric apparatus that includes an integrated array of detector elements that are at least generally aligned in at least a first direction, and that are responsive to incident radiation to produce an output signal that includes information from the incident radiation, at least one spectrally selective element, and a plurality of separate optical channeling elements positioned in optical paths that pass through at least part of the spectrally selective elements and on to different detector elements in the array.

In preferred embodiments, there can be a single spectrally sensitive element between the array and the optical channeling elements. The spectrally selective element can be a variable filter having spectral characteristics that vary along at least along the first direction. The optical channeling elements can include optical fibers that are each optically coupled to a subset of the detector elements. The optical fibers can be each optically coupled to a subset of the detector elements through areas of the variable filter having different spectral characteristics. The apparatus can further include a cylindrical lens disposed between the optical fibers and the variable filter with the axis of curvature of the cylindrical lens being perpendicular to the first direction. Ends of the fibers can be physically coupled to the filter. The fibers can be mounted directly to the variable filter. The fibers can be separately routed to different locations within an apparatus carrying out a process. The integrated array can be an array of infrared detector elements that are responsive to incident infrared radiation to produce the output signal. The integrated array can be an array of ultraviolet detector elements that are responsive to incident ultraviolet radiation to produce the output signal. The integrated array can be an array of visible-range detector elements that are responsive to incident visible light to produce the output signal. The apparatus can further include a narrow-band source with the detector array and the variable filter being operative on wavelengths outside of the bandwidth of the source. The detector array can be a two-dimensional detector array.

In another general aspect, the invention features a monitoring method that includes collecting radiation from a plurality of different locations through a plurality of different optical channels, channeling the radiation through the channels, and directing the radiation from each of the channels to a subset of the detectors in an integrated array detector.

In preferred embodiments, the step of directing can direct the radiation though a variable filter. The method can further include the step of filtering portions of the radiation from each of the channels with different spectral characteristics. The step of collecting can collect infrared radiation. The step of collecting can collect ultraviolet radiation. The step of collecting can collect visible radiation. The step of collecting collects wavelengths outside of a bandwidth of a source. The step of collecting can collect a two-dimensional image.

In a further general aspect, the invention features a spectrometric method that includes receiving radiation from a plurality of portions of a sample, and detecting the radiation at a two-dimensional plurality of locations corresponding to the plurality of locations through a plurality of parallel paths.

In preferred embodiments, the method can further include a step of filtering the radiation in the different paths with different spectral characteristics. The method can further include a step of holding the sample in a vessel.

In another general aspect, the invention features a spectrometric method that includes indirectly driving a sample in a first direction, filtering radiation that interacts with the sample with different spectral characteristics as the sample is driven by the step of driving, and acquiring images of the filtered radiation.

In preferred embodiments, the step of indirectly driving can be performed by passively driving the sample. The step of indirectly driving can be incidental to a process being performed for the sample.

In a further general aspect, the invention features a spectroscopic method that includes providing a pattern in a spatial-spectral coordinate space, acquiring spectral image signals from an array of radiation detector elements for a series of different wavelengths, and comparing the spectral image signals acquired in the step of acquiring with the pattern provided in the step of providing.

In preferred embodiments, the step of acquiring can take place through a variable filter having spectral characteristics that vary in at least one direction, with the step of providing a pattern providing a pattern designed to compensate for the spectral characteristics. The method can further include a step of filtering radiation before it reaches the array of radiation detectors. The step of filtering radiation can be performed with a piece of known-good sample material. The pattern can result from an acquired spectral data set. The steps of acquiring and comparing can be repeated as a plurality of samples is being mixed. The method can further include a step of providing an output signal when the one of the steps of comparing indicates that the sample is adequately mixed. The step of comparing can include an image subtraction. The step of comparing can be repeated for a plurality of patterns. The step of comparing can be repeated for a lower bound pattern and an upper bound pattern. The step of comparing can be repeated for patterns corresponding to different chemical species. The method can further include a step of moving a composition through a series of optical paths that each also pass through the filter and reach the detector to obtain the series of detector signals. The step of moving can move the composition in a series of discrete spatial areas. The method can be applied to a pharmaceutical composition, with the series of discrete spatial areas being dosage units of the pharmaceutical composition. Points on the surface can each define an intensity limit at one of a series of different wavelengths. The steps of acquiring and comparing can each be performed twice, at 90 degree angles with respect to each other. The step of providing a pattern can provide a two-dimensional surface. The step of acquiring can acquire infrared spectral image signals. The step of acquiring can acquire ultraviolet spectral image signals. The step of acquiring can acquire visible spectral image signals. The step of acquiring can acquire wavelengths outside of a bandwidth of a source. The step of acquiring can acquire a two-dimensional image.

In another general aspect, the invention features a spectrometric apparatus that includes a detector responsive to radiation incident on a sample from a radiation source, a spectrally selective element between the source and detector, and a comparator responsive to the detector and to a pattern corresponding to a spatial distribution of wavelengths.

In preferred embodiments, the apparatus can further include a variable filter having spectral characteristics that vary in at least one direction, and wherein the pattern is designed to compensate for the spectral characteristics. The apparatus can further include a filter between the source and the detector. The filter can include known-good sample material. The apparatus can further include automatic mixing monitoring logic having an output that is operative to provide a signal when the sample is adequately mixed. The comparator can be a dual-threshold comparator. The detector can be an infrared detector that is responsive to incident infrared radiation. The detector can be an ultraviolet detector that is responsive to ultraviolet infrared radiation. The detector can be a visible detector that is responsive to incident visible radiation. The apparatus can further include a narrow-band source and wherein the detector is operative on wavelengths outside of a bandwidth of the source. The detector can be a two-dimensional detector array. The spectrally selective element can be a variable filter. The variable filter can be a variable band-pass filter. The variable filter can be a continuously variable filter. The apparatus can further include multivariate spectral analysis logic responsive to the detector.

In a further general aspect, the invention features a spectrometric apparatus that includes a first two-dimensional set of detector elements that are at least generally aligned in a first direction and a second direction at least generally perpendicular to the first direction, a second two-dimensional set of detector elements that are at least generally aligned in a third direction and a fourth direction at least generally perpendicular to the first direction, a first variable filter portion in a first optical path between a sample and the first set of detector elements and having spectral characteristics that vary along at least the first direction, and a second variable filter portion in a second optical path between a sample and the first set of detector elements and having spectral characteristics that vary along at least the fourth direction, wherein the direction of change of spectral characteristics of the first variable filter is at least generally perpendicular to the direction of change of spectral characteristics of the second variable filter in reference to the orientation of the sample as conveyed by the optical paths.

In preferred embodiments, the first and second sets of detector elements can form part of a same array, with the first and third directions being the same, and with the second and fourth directions being the same. The apparatus can further include first and second filter portions in the first and second optical paths, respectively, with the first and second filter portions including known-good sample material. The apparatus can further include an optical arrangement to create the first and second optical paths from the sample. The optical arrangement can include a beam splitter. The apparatus can further include automatic mixing monitoring logic having an output that is operative to provide a signal when the sample is adequately mixed. The detector elements can be infrared detector elements that are responsive to incident infrared radiation. The detector elements can be ultraviolet detector elements that are responsive to incident ultraviolet radiation. The detector elements can be visible detector elements that are responsive to incident visible radiation. The apparatus can further include a narrow-band source, with the detector elements being operative on wavelengths outside of the bandwidth of the source. The variable filter portions can be variable band-pass filter portions. The variable filter portions can be continuously variable filter portions. The apparatus can further include including multivariate spectral analysis logic responsive to the detector elements.

In another general aspect, the invention features a spectrometric method that includes a first step of filtering radiation received from a sample, wherein a direction of variation of spectral filtering characteristics varies along a first axis with respect to an orientation of the sample, a second step of filtering radiation received from a sample, wherein a direction of variation of spectral filtering characteristics varies along a second axis with respect to an orientation of the sample, wherein the first and second axes are at least generally perpendicular, and acquiring spectral images of the radiation filtered in the steps of filtering.

In preferred embodiments, the steps of filtering can take place substantially simultaneously, with the step of acquiring spectral images acquiring image data from the first and second filtering steps, and can further include a step of splitting an optical path to provide the radiation for the first step of filtering and for the second step of filtering.

In a further general aspect, the invention features a spectroscopic method that includes acquiring a three-dimensional set of spectral image signals from an array of radiation detectors for a series of different wavelengths, a first step of correcting for differences in intensity for at least a first subset of the signals, and a first step of correcting for differences in spectral variability for at least a first subset of the signals.

In preferred embodiments, the method can further include the steps of assembling results of the steps of acquiring, correcting for differences in intensity, and correcting for differences in spectral variability into a first spectral image. The method can further include a second step of correcting for differences in intensity for at least a second subset of the signals, and further include a second step of correcting for differences in spectral variability for at least a second subset of the signals, and further include the step of assembling results of the step of acquiring, the first and second steps of correcting for differences in intensity, and the first and second steps of correcting for differences in spectral variability into a second spectral image. The first step of correcting for differences in intensity and the first step of correcting for differences in spectral variability can be performed using a same set of factors for spectrally different subsets of the three-dimensional set of spectral image signals. The step of correcting for differences in intensity can include adjusting received intensity values based on a set of intensity correction factors. The step of correcting for differences in intensity can be performed by a matrix operation on a matrix of intensity values and a score matrix. The step of correcting for differences in spectral variability can include adjusting received intensity values at different wavelengths based on a set of spectral variability correction factors. The step of correcting can be performed by a matrix operation on a matrix of intensity values and a loading vector. The steps of correcting can be performed simultaneously in a single matrix operation. The steps of correcting can be performed by adjusting a sample data cube with a calibration data cube that is based on an expansion of a set of score values and a set of loading values. Factors employed in the first step of correcting for differences in intensity and the first step of correcting for differences in spectral variability can be derived using principal component analysis. The step of correcting for differences in intensity can take place using substantially fewer values than there are pixel values in the image signals. The step of correcting for differences in spectral variability can take place using substantially fewer values than there are pixel values in the image signals. The steps of correcting for differences in intensity and spectral variability taken together can use substantially fewer values than there are pixel values in the image signals. The step of acquiring can acquire infrared spectral image signals. The step of acquiring can acquire ultraviolet spectral image signals. The step of acquiring can acquire visible spectral image signals. The step of acquiring can acquire wavelengths outside of a bandwidth of a source.

In another general aspect, the invention features a spectroscopic method that includes obtaining a background calibration data set, deriving a set of intensity correction values from the background calibration data set, deriving a set of spectral variability correction values from the background calibration data set, and calibrating at least one acquired image data set based on the intensity correction values and spectral variability values derived in the steps of deriving.

In preferred embodiments, the steps of deriving can operate according to principles of principal component analysis.

In a further general aspect, the invention features a spectrometric apparatus that includes a spectrally selective element, a detector array including a plurality of detector elements and being responsive to radiation from a source that has passed through the spectrally selective element, and calibration logic responsive to the detector array and including intensity correction logic and spectral variability logic.

In another general aspect, the invention features a spectrometric apparatus that includes an infrared illumination source directed toward a sample, a plurality of detector elements that are responsive to infrared radiation scattered from the sample to produce an output signal that includes information from the incident radiation, and an analysis module responsive to the output signal from the detector elements and operative to analyze spatial distribution of information received by the array.

In preferred embodiments, the sample can be a heterogeneous powder and further the apparatus can further include a vessel to hold the sample. The apparatus can further include mixing machinery operatively connected to the vessel to mix the sample. The mixing machinery can include an input responsive to the analysis module. The analysis module can include logic operative to analyze scattering. The analysis module can include logic operative to detect a stable state. The apparatus can further include a second source having spectral characteristics that are different from those of the first source. The analysis module can be operative to derive both chemical and size information from the scattered radiation, with the analysis module being operative to derive the chemical information from differences between the output signals resulting from illumination by the first and second sources.

The apparatus can further include source control logic operative to alternate the illumination of the sources. The source can be a pulsed laser diode. The source can be a coherent source. The analysis module can be operative to analyze particle size. The analysis module can be operative to analyze changes in particle size. The analysis module can be operative to analyze the growth of particles as a function of time during granulation. The plurality of detectors can form part of a two-dimensional integrated detector array. The analysis module can be operative to derive both chemical and size information from the scattered radiation. The source and detector can be operative in the near-infrared range.

In a further general aspect, the invention features a spectrometric detection method that includes illuminating a sample with infrared light, acquiring a spectral image of a scattered image pattern resulting from the step of illuminating; and analyzing a spatial distribution of the scattered spectral image pattern. The sample can be a heterogeneous powder and further including a vessel to hold the sample. The method can further include the step of inducing motion in the sample. The method can further include the step of detecting a stable state in the sample. The step of illuminating can illuminate with first and second different spectral characteristics, with the step of analyzing obtaining chemical information from differences between interactions between the sample and the first and second different spectral characteristics.

In preferred embodiments, the step of analyzing can include analyzing particle size. The step of analyzing can include analyzing changes in particle size. The step of analyzing can include analyzing the growth of particles as a function of time during granulation. The step of acquiring can be performed by a two-dimensional integrated detector array. The step of analyzing can include deriving both chemical and size distribution information from the scattered radiation. The steps of illuminating and detecting can both take place in the near-infrared range.

In another general aspect, the invention features a spectrometric apparatus that includes means for illuminating a sample with infrared light, means for acquiring a spectral image of a scattered image pattern resulting from the means for illuminating; and means for analyzing a spatial distribution of the scattered spectral image pattern.

Systems according to the invention may be advantageous in that they can employ direct coupling of radiation to an imaging array to robustly and inexpensively achieve high-performance spectral imaging characteristics. Because such systems do not require an expensive first-stage optic, they can be made less expensively than comparable systems that do require one. And the lack of a first stage optic, which might otherwise be broken, scratched, and/or knocked out of alignment, also makes systems according to the invention more robust. In addition, by designing such systems to take advantage of passive or incidental motive forces, they can be built entirely without moving parts or at least without additional moving parts, making them even more inexpensive and robust.

Systems according to the invention can also be used in distributed ways to achieve further cost savings. By directly monitoring a series of positions in a process or system with a single array, systems according to the invention can perform a number of operations that might otherwise require several spectrometers. This can result in savings in instrument manufacturing, installation, and monitoring costs.

Systems according to the invention may also benefit from direct deposition of a variable filter coating on an imaging array. This arrangement yields a simple, inexpensive and robust spectral imaging combination that is quite versatile. And by performing the deposition at the time of manufacture of the array, the system can be made particularly inexpensively.

Systems according to the invention may be able to derive spectral-spatial information from their targets as well. This information can allow for the detection of poorly mixed or counterfeit pharmaceuticals or other items. And because the information is derived through preprogrammed analysis logic, the result can be made to be completely objective.

Spatial capabilities of the system can also be used to perform trace analysis. By deliberately distributing a received sample over a large area, the presence of small amounts of contaminants can be detected, even if their concentration is very low and would otherwise require a system with a high degree of precision. And the sensitivity of this technique can be easily enhanced by simply increasing the degree of spreading of the material.

Systems according to the invention can also benefit from spatial-spectral pattern analysis. This approach allows spectral patterns to be simply acquired from known-good materials, and then compared with acquired images using simple comparison operations. Contaminant detection and other spectroscopic and spectrometric operations can therefore be set up and performed quickly and reliably.

And the use of the spectra of known-good materials as well as actual known-good materials as filters provides further benefits. Such filters can be easily mated to equipment, without any preliminary computations. They then cause other materials to stand out in the field of view of the array. And they provide for the direct extraction of spatial distribution information for the material, allowing for efficient and accurate monitoring of mixing of ingredients.

Systems according to the invention can further exhibit enhanced noise rejection. By extracting loading and score information from a calibration set, spatially distributed noise can be dropped from calibration computations. This approach can also speed up calibration computations by storing calibration information in a less redundant format.

DESCRIPTION OF AN ILLUSTRATIVE EMBODIMENT

Figure 1:
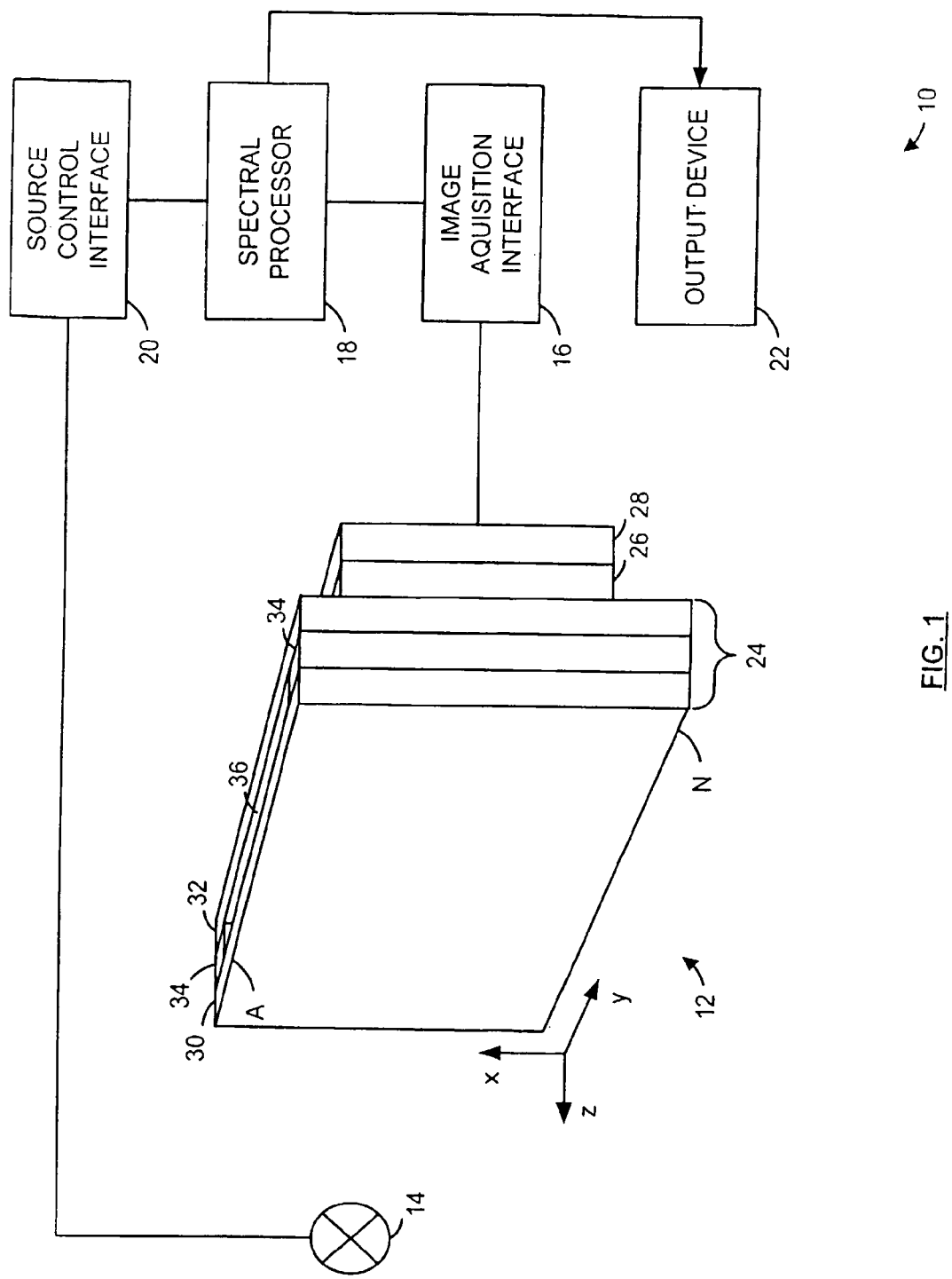
FIG. 1 is a diagram of an illustrative embodiment of a spectrometric system according to the invention, including a perspective portion illustrating its acquisition unit.

Referring to FIG. 1, a spectrometric system 10 according to the invention includes an acquisition unit 12 located within range of a radiation source 14. The acquisition unit is operatively connected to an acquisition interface 16, which is in turn operatively connected to a spectral processor 18. The spectral processor has an output operatively connected to an input of an output device 22. The radiation source can be operatively connected to a source control interface 20, which is in turn coupled to the spectral processor, although in some instances, separately driven or even ambient light sources may be used instead. And while in this embodiment the elements of the system are optimized for use in the near-infrared spectral region, techniques according to the invention can also be applied to other spectral regions, such as the ultraviolet, visible, or far-infrared regions.

The acquisition unit 12 can be implemented as a sandwich that includes a sample vessel 24, a variable filter 26, and detector array 28. The vessel can be butted up against the variable filter and it can overlap some or all of the field of view of the array. In this embodiment, the vessel includes side walls 30, 32 and end walls 34 that surround a process flow being monitored for traces of contaminants. The vessel can also be one of a number of other types of vessels that serve a number of other functions. It can be a mixing vessel in which disparate ingredients are being mixed. Or it can be a liquid chromatography vessel with the side walls 30, 32 and end walls 34 surrounding an adequate amount of adsorbing medium 36, such as a mass of beads, to form an effective chromatography column that can separate liquids, gases, or dissolved substances. This chromatography vessel can also be exposed to a bias gradient perpendicular to its axis of elution (x), such as temperature or pH gradient.

The filter 26 is preferably a filter with variable characteristics, such as one with a narrow pass-band and a center wavelength that varies along one direction. A first edge A of such a filter passes a narrow range of shorter wavelengths, and as the distance from the first edge along the process flow direction increases, it passes successively longer wavelengths. At the second edge N of the filter, the filter passes a narrow range of the longest wavelengths. The orientation of the filter can also be reversed, so that the pass-band center wavelength decreases from the first edge to the second edge. Although the filter can be made up of a series of strips, it can also be manufactured by continuously varying the dielectric thickness in an interference filter. Preferably, the filter should have a range of pass-bands that matches the range of the array. Suitable filters are available, for example, from Optical Coatings Laboratory, Inc. of Santa Rosa, Calif. Although the variable filter is shown between the sample and the detector array, in other embodiments it can also be located between the source and sample.

The detector array 28, filter 26, and vessel 24 can be directly coupled. In a directly coupled configuration the sample is in optical proximity with the detector array, allowing individual elements of the detector array to receive radiation from relatively small areas of the sample via parallel optical paths (e.g., along the z axis in FIG. 1). There is therefore no need for a first-stage optic to collimate or focus the radiation, allowing the system to be less expensive and more robust.

It will be apparent to one of skill in the art that FIG. 1 is designed as a conceptual presentation and its depiction of the acquisition unit is therefore not to scale. In practice, the different elements can vary significantly in their dimensions and relative positions. The variable filter can be made up of a series of thin coatings on the order of infrared wavelengths, for example, while the vessel can be made up of relatively thick glass on the order of several millimeters. The size, shape, and material characteristics of the elements of the acquisition unit may also depend on the application to which the system is being applied.

Figure 2:
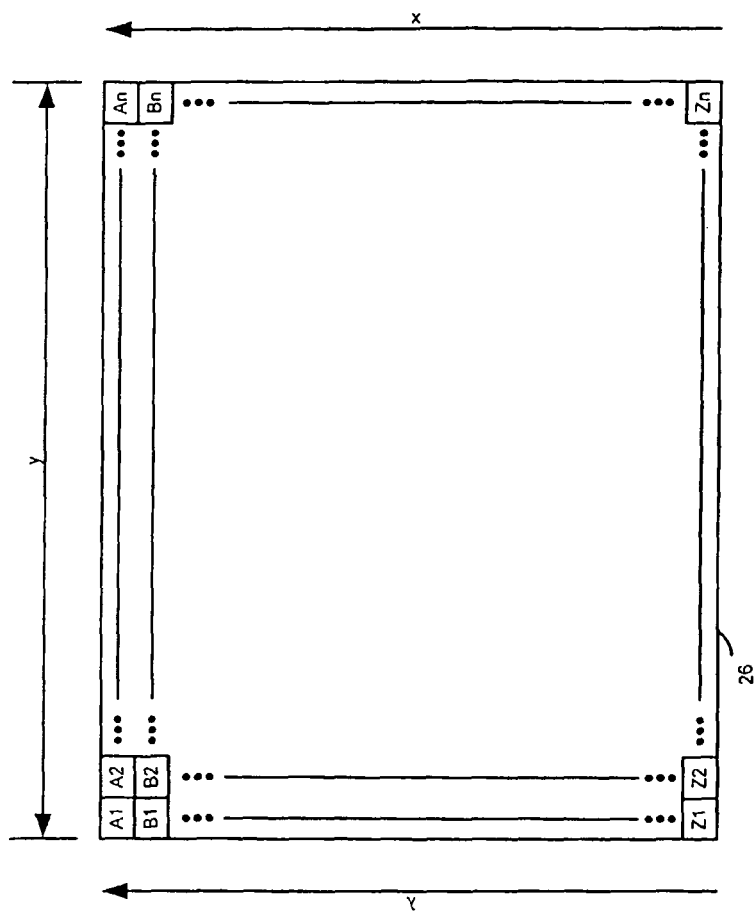
FIG. 2 is a plan view diagram of an image sensor for use with the process control system of FIG. 1.

Referring also to FIG. 2, the detector array 28 is preferably a two-dimensional array sensor that includes a two-dimensional array of detector elements made up of a series of lines of elements (A1-An, B1-Bn, . . . , Z1-Zn) that are each located generally along an axis that is perpendicular to the spatial distribution of sample elements. The image sensor can include an array of integrated semiconductor elements, and can be sensitive to near infrared radiation. Other types of detectors can also be used, however, such as CCD detectors that are sensitive to ultraviolet light, visible light, or far-infrared light. For near infrared applications, uncooled two-dimensional Indium-Gallium-Arsenide (InGaAs) arrays, which are sensitive to near-infrared wavelengths, are suitable image sensors, although sensitivity to longer wavelengths, such as is available from Mercury-Cadmium-Telluride (MCT) detectors would also be desirable. It is contemplated that the sensors should preferably have dimensions of at least 64×64 or even 256×256.

The image acquisition interface 16 has an input port responsive to an output port of the detector array 28, and it receives and/or formats image signals it receives from the detector on this input port. It can include an off-the shelf frame grabber/buffer card with a 12-16 bit dynamic range, such as are available from Matrox Electronic Systems Ltd. of Montreal, Canada, and Dipix Technologies, of Ottawa, Canada.

The spectral processor 18 has an input responsive to the image acquisition interface 16. It also has a control output provided to a source control interface 20 that can power and control the source 14, which can be placed to reflect light off the sample or transmit light through the sample. The illumination source for near-infrared measurements is preferably a Quartz-Tungsten-Halogen lamp. For Raman measurements, the source may be a coherent narrow band excitation source such as a laser. Other sources can of course also be used for measurements made in other wavelength ranges, and light from uncontrolled, ambient sources may even be appropriate in some instances.

The spectral processor 18 can also be operatively connected to a standard input/output (IO) interface, and may be connected to a local spectral library as well (not shown). The local spectral library can include locally-stored spectral signatures for substances, such as known process components. These components can include commonly detected substances or substances expected to be detected, such as ingredients, process products, or results of process defects or contamination. The IO interface can also operatively connect the spectral processor to a remote spectral library.

The spectral processor 18 may include or be operatively connected to additional signal processing logic. This logic can include an off-the-shelf programmable industrial image processor with special-purpose image processing hardware and image evaluation routines that are operative to evaluate shapes and colors in the sample vessel. Such systems are available from, for example, Cognex, Inc.

In one embodiment, the system is based on the so-called IBM-PC architecture, with the image acquisition interface 16 and image processor each occupying expansion slots on the system bus. The spectral processor is implemented using special-purpose spectral processing routines loaded on the host processor, and the local spectral library is stored in local mass storage, such as disk storage. Of course, other structures can be used to implement systems according to the invention, including various combinations of dedicated hardware and special-purpose software running on general-purpose hardware. In addition, the various elements and steps described can be reorganized, divided, and combined in different ways without departing from the scope and spirit of the invention. For example, many of the separate operations described above can be performed simultaneously according to well-known pipelining and parallel processing principles.

Figure 3:
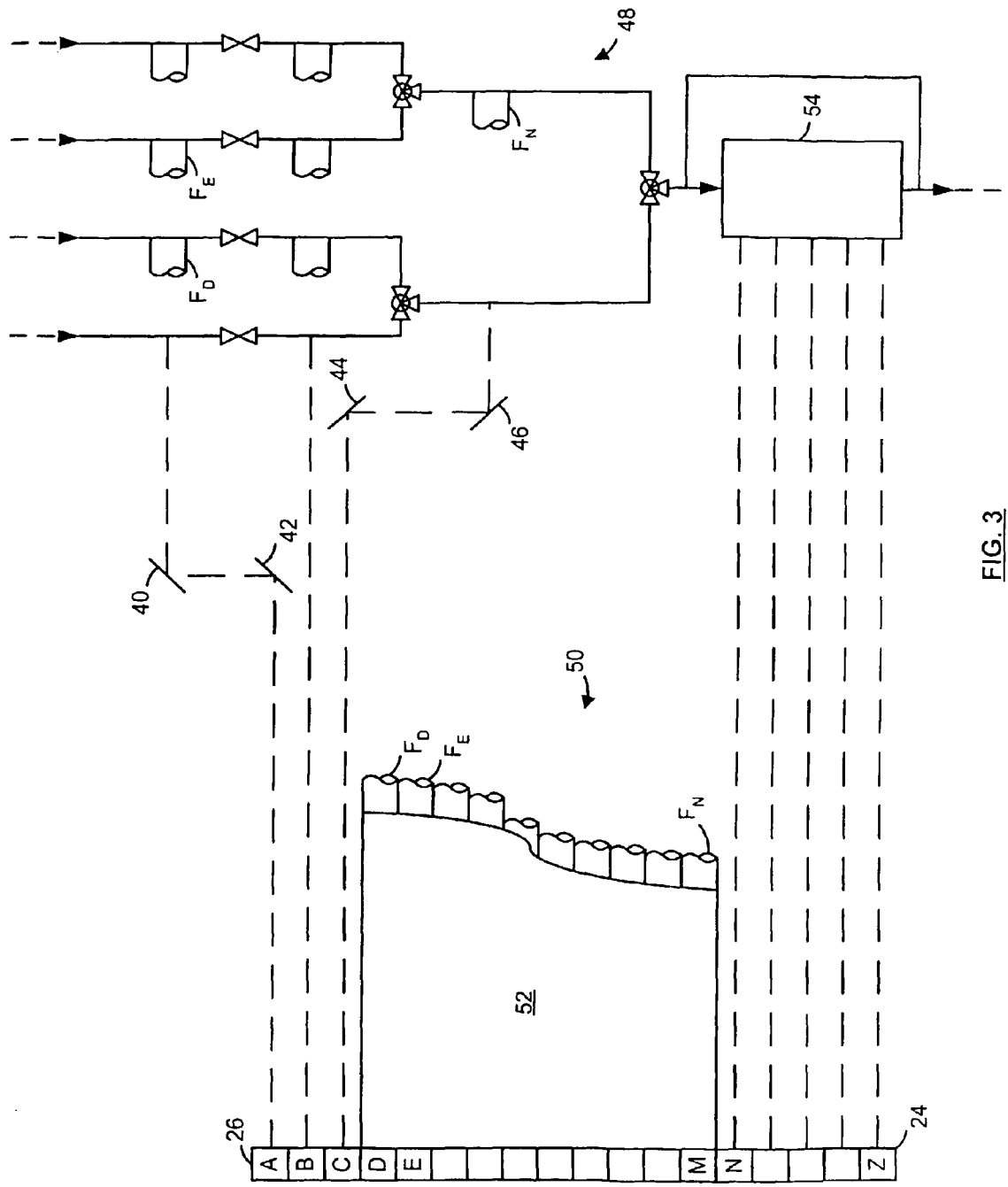
FIG. 3 is a schematic diagram of a distributed spectrometric process monitoring system according to the invention.

Referring to FIG. 3, portions of the array can be coupled to more than one vessel or other observation point in a process. In one embodiment, for example, a first row A of a detector array is exposed to radiation reflected by a first set of mirrors 40, 42 from a first observation point in a fluid conveying network 48 carrying out a process. A second row B is exposed to radiation shining directly from a second observation point in the process network. A third row C is exposed to radiation reflected by a second set of mirrors 44, 46 from a third observation point in the process network.

A number of the rows of the array D, E, . . . M, are exposed to radiation conveyed from further observation points in the process network via optical fibers $F_D$, $F_E$, ... $F_N$. These fibers may be individual fibers or they may be part of a bundle 50 held together by a sheath 52 for at least part of their length.

The fibers can be coupled to the array in a variety of ways. In one embodiment, the array 28 itself is coated with successive layers of variable thickness to form a variable filter 26 on the array, making each row of the array sensitive to a number of different wavelengths. Radiation received from each fiber can then be spread out over one of the rows using a cylindrical lens, a mirror, waveguides, or other optical elements.

In other embodiments, the variable filter can be based on other patterns. Where the filter is deposited directly on the array, for example, individual pixels may be coated with coatings of different thicknesses. This can allow small areas that are comparable to the dimensions of single fiber to be sensitive to a whole range of wavelengths. Ends of the fibers can then be butted directly against those areas in the coated array.

The remaining rows of the array N-Z can be exposed to a spreading element 54 to enable trace analysis. The spreading element is designed to disperse some or all of a process stream over a relatively large area. In the case of a fluid, such as slurry or suspension, the spreading element can be a large, flat, transparent conduit located in front of the detector array and filter. A liquid stream can also be aerosolized to achieve adequate spreading. Solid flows, such as pellets or grain, can be dispersed onto wider conveyor belt areas using obstacles and/or vibrating elements. They can also be dispersed into a spray by forceful ejection and imaged in mid-air. Other suitable spreading implements can be developed depending on the needs of the system. These elements can be applied to the whole process stream to ensure that no contaminants are present, or they can be applied to a portion of the process stream to effectively sample the process stream. Trace analysis logic can be provided within or in addition to the spectral processor to process signals received from the spreading element.

Figure 4:
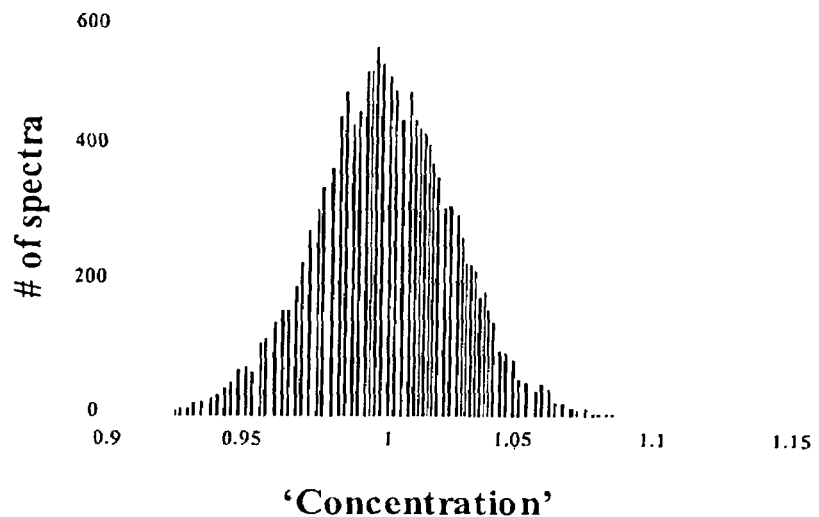
FIG. 4 is a plot of the frequency distribution of concentration over the area of a machine-mixed pharmaceutical tablet.

Referring to FIG. 4, spectral-spatial analysis logic may also be included as part of or in addition to the spectral processor 18. The spectral-spatial analysis logic can include statistical analysis logic to determine statistical properties of the spectral-spatial information gathered by the detector array. This logic can provide its output in a variety of forms, including raw numbers, graphs, or images that can be presented on an output device, such as a display or printer. In process monitoring settings, the logic may also provide output signals that can be used for a variety of purposes, such as to adjust the process, reject an item or batch, or alert an operator.

Figure 5:
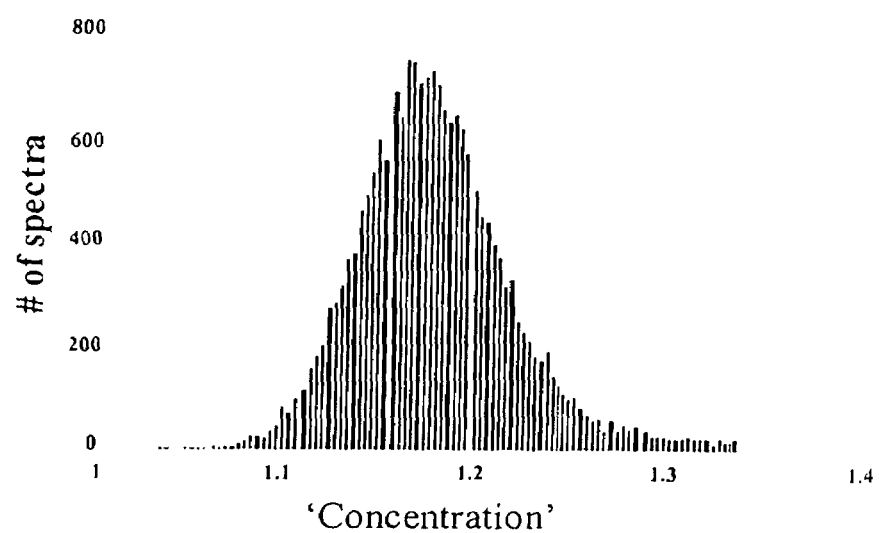
FIG. 5 is a plot of the frequency distribution of concentration over the area of a hand-mixed pharmaceutical tablet.
Figure 6:
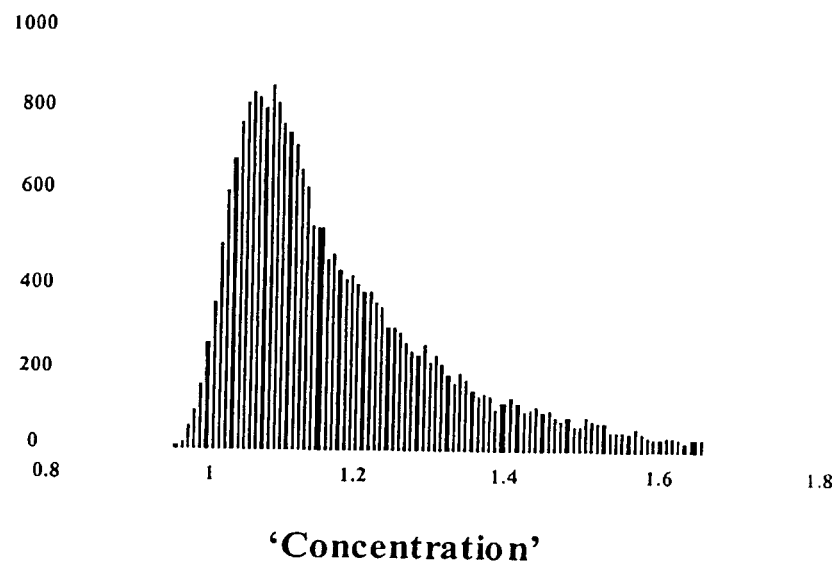
FIG. 6 is a plot of the frequency distribution of concentration over the area of a poorly mixed pharmaceutical tablet.
Figure 8:
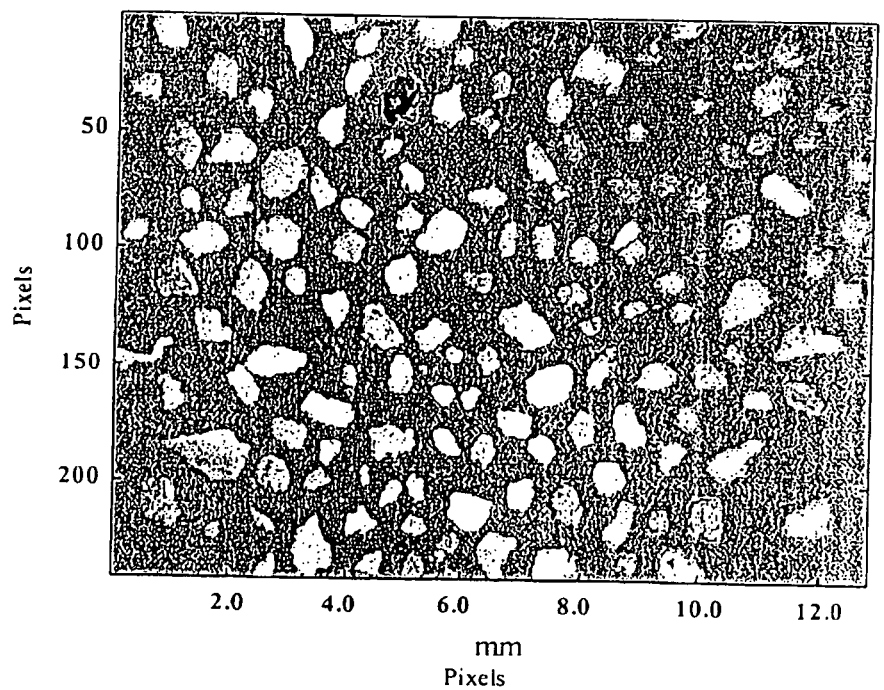
FIG. 8 is an spectral image of contaminated cattle feed.

The statistical analysis logic can derive and analyze the relative frequency distribution of concentration for one or more substances. This logic can present its output as a plot, as shown in FIGS. 4-6. It may also be processed to calculate a mean, skew, and/or kurtosis for the distribution. The mean provides an indication of the overall concentration or amount of an item or substance analyzed. In the case of a pharmaceutical dosage unit, for example, the mean provides a measure of its dosage. The standard deviation can provide for a measure of the range of variation of certain properties, such as film thickness. Skew and kurtosis both provide an indication of non-uniformity of mixing or non-normal statistical distribution in a sample. These quantities can be evaluated as absolute numbers or in comparison with earlier results. The statistical analysis logic can also perform its analysis on more than one chemical component or property, and it can detect and analyze overlapping distributions, such as by curve fitting.

In operation, referring to FIGS. 1-2, the array sensor 28 is sensitive to radiation from the source that has interacted with contents of the vessel. This radiation travels through the variable filter 26, but in embodiments in which the acquisition unit is directly coupled, the radiation does not need to be focused or collimated by a first stage optic, because of its proximity to the array. As the components move through the column, the acquisition interface 18 acquires data representing a series of variably-filtered, two-dimensional images. These two-dimensional images each include image values for the pixels in a series of adjacent lines in the sample area. Because of the action of the variable filter, the detected line images that make up each two-dimensional image will have a spectral content that varies along one of the image axes when viewing a heterogeneous field of view. Spectral content can vary with chemical content or other properties, such as film thickness.

Spectral images can be assembled in a two-stage process. The first stage of the process is an acquisition stage, which includes successive image acquisition steps for the sample over a period of time. This period is related to the speed of the process that drives the sample material in front of the filter and detector array. Where chromatographic processes are employed, for example, the acquisition rate can be relatively slow, and depends on the specific reagents that need to be separated and the chromatography parameters used to achieve this separation.

The use of a chromatography pump to drive the sample in front of the array is an example of an indirect driver that can be used to drive the sample, filter, detector array, or other optical elements with respect to each other. Indirect drivers can include passive processes, such as sedimentation, capillary action, viscous friction, evaporation, convection, or gravity, to drive the relative motion. Indirect processes can also include incidental drivers, such as chromatography pumps or heating elements, which have a process-related purpose other than to simply transport the sample. Where a dedicated actuator, such as a conveyor, is used in addition to or in lieu of an indirect process, the acquisition rate can be tied to the motion of the actuator, or it can be self-scanning. At the end of the first process stage, the system will have acquired a three-dimensional mixed spectral data set.

In the second stage, image data are extracted from the mixed spectral data set and processed. In the embodiment described, pure spectral images are extracted in the form of a series of line images acquired at different relative positions. Part or all of the data from the extracted line image data sets can then be assembled to obtain two-dimensional spectral images for all or part of the sample area and pure spectra for each pixel in the image.

The conversion can take place in a variety of different ways. In one approach, a whole data set can be acquired before processing begins. This set can then be processed to obtain spectral images at selected wavelengths. The system may also allow a user to interact with an exploratory mode, in which he or she can look at representations of any subset of the data. This can allow the user to zoom in to specific parts of the sample and look at wavelengths or wavelength combinations that may not have been contemplated before the scan.

Data can also be processed as scanning of the filter takes place. In this approach, data may be processed or discarded as they are acquired, or simply not retrieved from the detector to create an abbreviated data set. For example, the system may only acquire data for a certain subset of wavelengths or areas, it may begin spectral manipulations for data as they are acquired, or it may perform image processing functions, such as spatial low-pass filtering, on data as they are acquired. Adaptive scanning modes may also be possible in which the system changes its behavior based on detected signals. For example, the system can abort its scan and alert an operator if certain wavelength characteristics are not detected in a reference sample.

The data can be accumulated into a series of single-wavelength bit planes for the whole image, for example, with data from these bit planes being combined to derive spectral images. Data can also be acquired, processed, and displayed in one fully interleaved process, instead of in the two-stage approach discussed above. And data from the unprocessed data set can even be accessed directly on demand, such as in response to a user command to examine a particular part of the sample area, without reformatting the data as a whole. Often, the system will be interested in information from spectral regions corresponding to particular reagents, products, or known contaminants, and in this case, information can be extracted directly from the data cube for the wavelengths of interest.

Once the spectral images are assembled, the spectral processor 18 can evaluate them. This evaluation can include a variety of univariate and multivariate spectral manipulations. These can include comparing received spectral information with spectral signatures stored in the library, comparing received spectral information attributable to an unknown sample with information attributable to one or more reference samples, or evaluating simplified test functions, such as looking for the absence of a particular wavelength or combination of wavelengths. Multivariate spectral manipulations, including principal component analysis, are discussed in more detail in "Multivariate Image Analysis," by Paul Geladi and Hans, Grahn, available from John Wiley, ISBN No. 0-471-93001-6, which is herein incorporated by reference.

As a result of its evaluation, the spectral processor 18 may detect known components and/or unknown components, or perform other spectral operations. If an unknown component is detected, the system can record a spectral signature entry for the new component type in a local spectral library. The system can also attempt to identify the newly detected component in an extended or remote library, such as by accessing it through a telephone line or computer network. The system then flags the detection of the new component to the system operator, and reports any retrieved candidate identities.

The system can map the selected chemical information from different detected components into a color (such as grayscale) image. This image can then be displayed to the operator, or transferred to an image processor, which can evaluate shape and color of the sample or sample areas, issue rejection signals for rejected sample areas, and compile operation logs.

Where the system is applied to chromatography, an operator begins by introducing a sample fluid into the vessel 24. As the sample fluid progresses through the vessel along its elution axis (x), the components of the fluid tend to separate into bands individual species, and these are steadily drawn through the medium. As the bands are being drawn through the medium, the image acquisition interface 16 acquires successive images of the portion of the contents of the vessel. Because the filter has different characteristics at different positions, the chemical data acquired for a particular chemical species will be different as it progresses along the flow or elution axis. And if there is an external bias, such as a temperature or pH gradient across the vessel, the acquired data will also include information about the effect of this gradient on the different bands. As a result, the spectral processor will be able to collect and store a three-dimensional series of images (i.e., a hypercube) that can include the response of each of the bands for a progression of bias values at some or all of the filter's wavelength pass bands.

Once the full data set has been acquired it can be processed in a variety of ways using multivariate spectral analysis methods. These methods can be used to derive the spectra of each of the individual bands. Or they can be used to create images at particular wavelengths. More sophisticated chemical analyses may also be performed, such as the comparison of spectra with library values, the detection of spectral-spatial patterns in the image data, or the analysis of the spatial distribution of the bands.

Referring to FIG. 3, where portions of the array are coupled to more than one observation point in a process, the acquisition process can be fundamentally the same as it would be for a single field of view. If the chemical information required from the different observation points is the same, the whole image acquired by the array can be treated just as if it were received from a single observation point. If different chemical information is required or information is required at different rates, however, the acquisition interface can acquire more images and/or subsets of the information can be used for the different channels. If different spectral regions are of interest for different channels, for example, the acquisition interface need only acquire and store image data for those wavelength regions of interest for a particular area of the detector array. Alternatively, a first channel might require a sample rate that is higher than that of the rest of the channels. In this case, the acquisition interface can acquire image data at the higher rate, and the higher rate data can be analyzed for the first channel. The remaining channels can use data from alternate scans, with the remaining data being discarded or ignored. Some or all of the channels can also be multiplexed, such as with shutters or moving mirrors. This can allow for the interleaved acquisition of data from a number of slower channels on some parts of the array, while individual, faster channels are serviced individually on other parts of the array.

Referring to FIGS. 4-6, the spectral-spatial information in the image data can also be analyzed. The following example outlines an experiment demonstrating this type of operation.

Example 1

Three tablets including the same active therapeutic ingredient (furosemide) and an inert crystalline cellulose excipient ("Avicel") were prepared. The first was blended using commercial equipment, such as would be normally used in large-scale manufacturing. The second was blended by hand. The third was deliberately poorly blended by hand in an attempt to simulate substandard manufacturing processes or counterfeit tablets.

Image data cubes having a resolution of 320×240 pixels were acquired for the three tablets using an array detector and a Liquid Chrystal Variable Filter (LCTF) with a scan range of 1050-1700 nm and a spectral resolution of 6 nm (76,800 spectra). The image data cubes were each processed using principal component analysis to extract a chemical image plane corresponding to the distribution and abundance of the active ingredient. The relative frequency distribution of the concentration of the active ingredient were derived and plotted for the three tablets, and these plots are presented in FIGS. 4, 5, and 6 respectively.

The first plot shows a normal symmetrical distribution with a mean of 1.0. This distribution indicates that the active ingredient was well mixed in the tablet. The mean shows that the tablet has a dose value of 1.0.

The second plot shows a slightly asymmetric distribution. Specifically, this plot exhibits a slight positive skew caused by the contribution of large unmixed areas in the hand-made tablet. The mean shows that the tablet has a dose value of 1.2. Not only is this tablet somewhat uneven, therefore, it also has 20% more active ingredient than it should.

The third plot shows a more skewed distribution. Like the second plot, this one exhibits a positive skew, but the skew is significantly more pronounced in this distribution than it was in the second plot. This higher skew confirms that the third tablet is more poorly mixed than the first. The mean for the third tablet shows that this tablet also has a dose value of 1.2.

Figure 7:
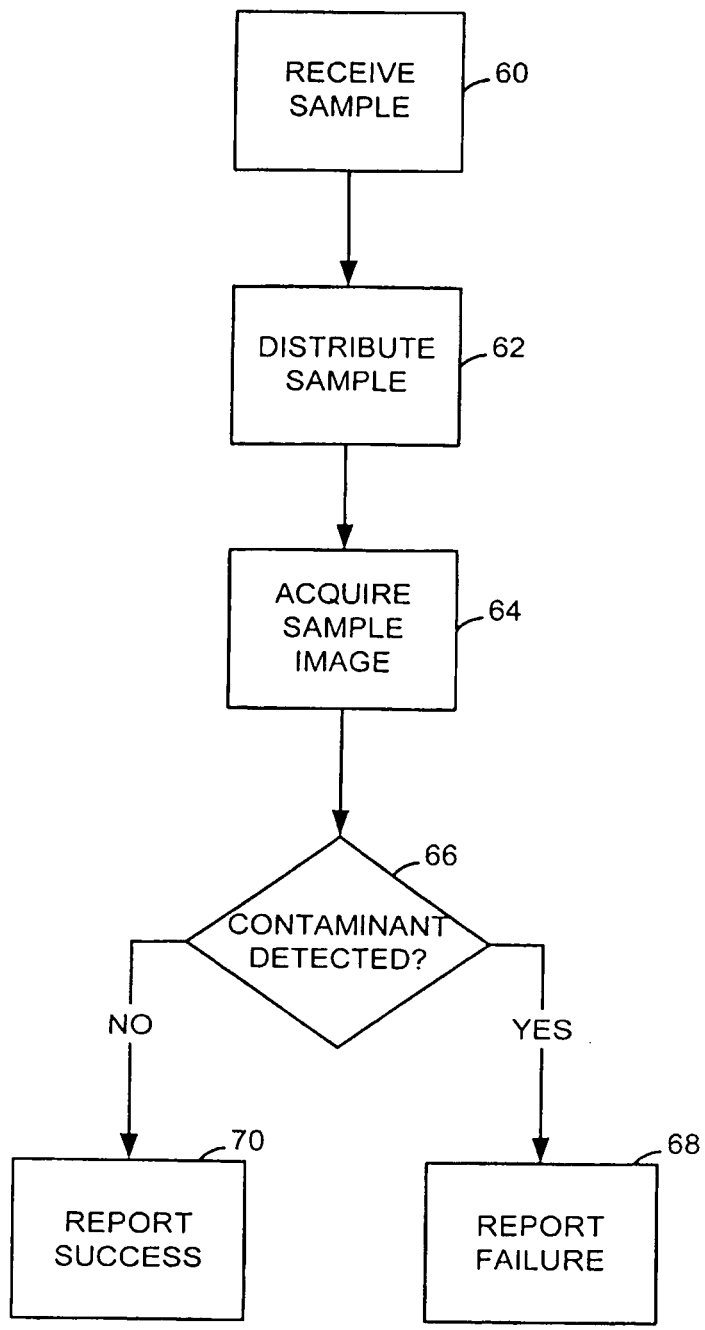
FIG. 7 is a flowchart for trace analysis using a system such as is shown in FIGS. 1-3.

Referring to FIG. 7, the spatial capabilities of the system 10 can also allow for trace analysis in heterogeneous materials or materials for which samples can be made to be heterogeneous. This approach involves deliberately distributing a received sample over a larger area such as with a spreading element 54 (step 62). The system then acquires an image of the sample (step 64). If the trace analysis logic detects a contaminant in any region of the distributed sample (step 66), therefore, its presence can be reported (step 68) or its absence confirmed (step 70). This technique has the advantage that its sensitivity can be enhanced by simply increasing the degree of spreading of the material. The following example illustrates the application of this technique.

Example 2

A contaminant particle of animal protein was added to a small batch of vegetable-based cattle feed. The mixture was then spread out over an area of about 250 mm×12.5 mm and an image data cube having a resolution of 320×240 pixels was acquired using an array detector and a Liquid Chrystal Variable Filter (LCTF) with a scan range of 1050-1700 nm and a spectral resolution of 6 nm (76,800 spectra). The image data cube was processed using principal component analysis to extract a chemical image plane for the vegetable-based cattle feed. The processed image clearly shows the contaminant despite the fact that it makes up a small portion of the detector's field of view. This technique can therefore provide a powerful form of trace analysis using relatively inexpensive detection equipment.

Figure 9:
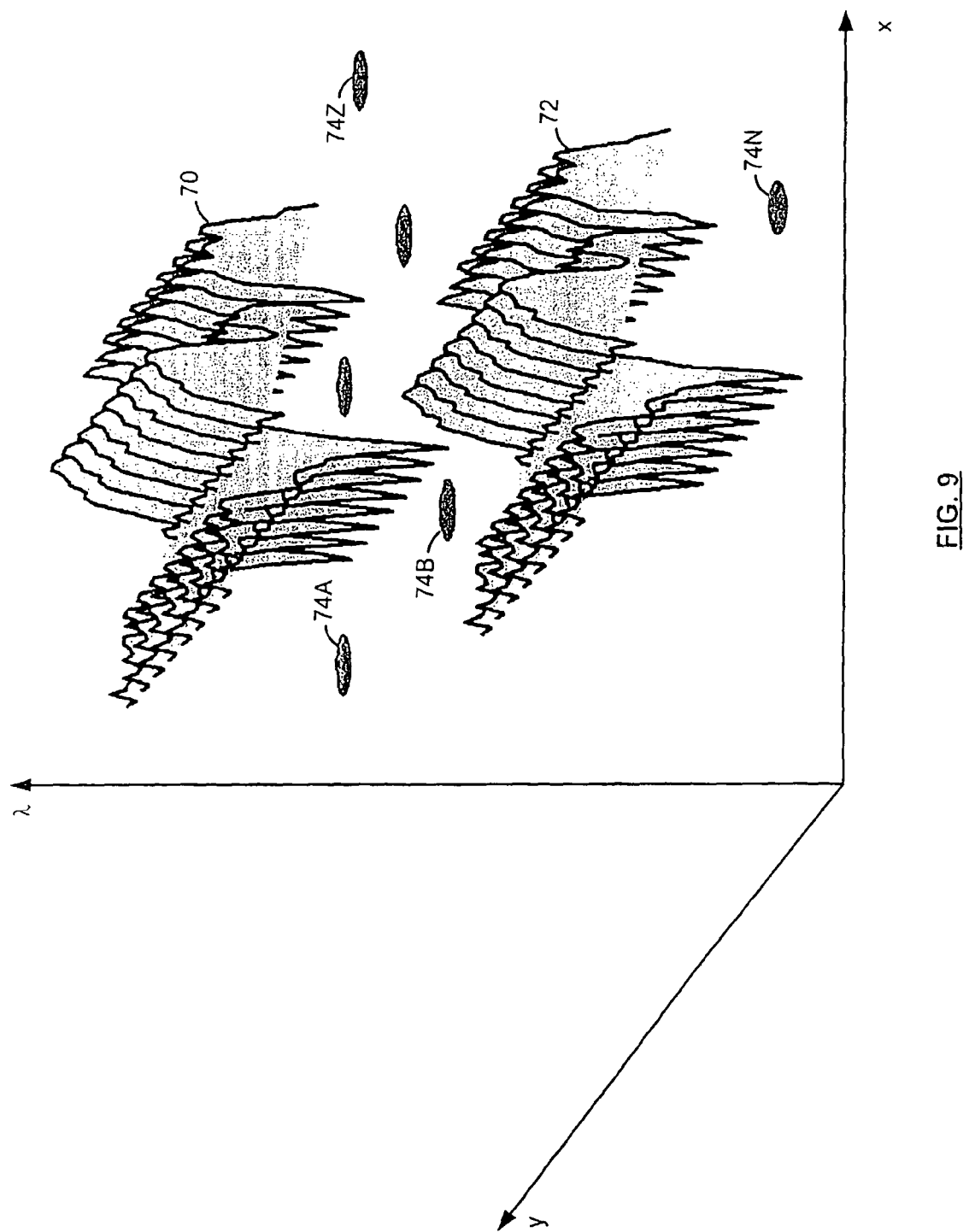
FIG. 9 is a three-dimensional rendering of upper and lower bound surfaces and a series of sample items shown in spectral-spatial space.

Referring to FIGS. 1 and 9, spectral-spatial pattern recognition logic can also be provided within or in addition to the spectral processor 18. This logic receives spectral data acquired by the acquisition interface 16 and compares it with one or more stored spectral-spatial patterns. Spectral-spatial patterns are patterns in a spectral-spatial coordinate system. For example, spectral-spatial patterns can be three-dimensional surfaces 70, 72 in x-y-λ space, with x being a spatial coordinate coincident with a direction of change of wavelength of the variable filter 26, y being a spatial coordinate coincident with another dimension of the filter, and λ being a wavelength coordinate. This spectral surface can be a multivariate surface matched to the characteristics of the variable filter, allowing for direct comparisons between the surface and acquired data.

Figure 10:
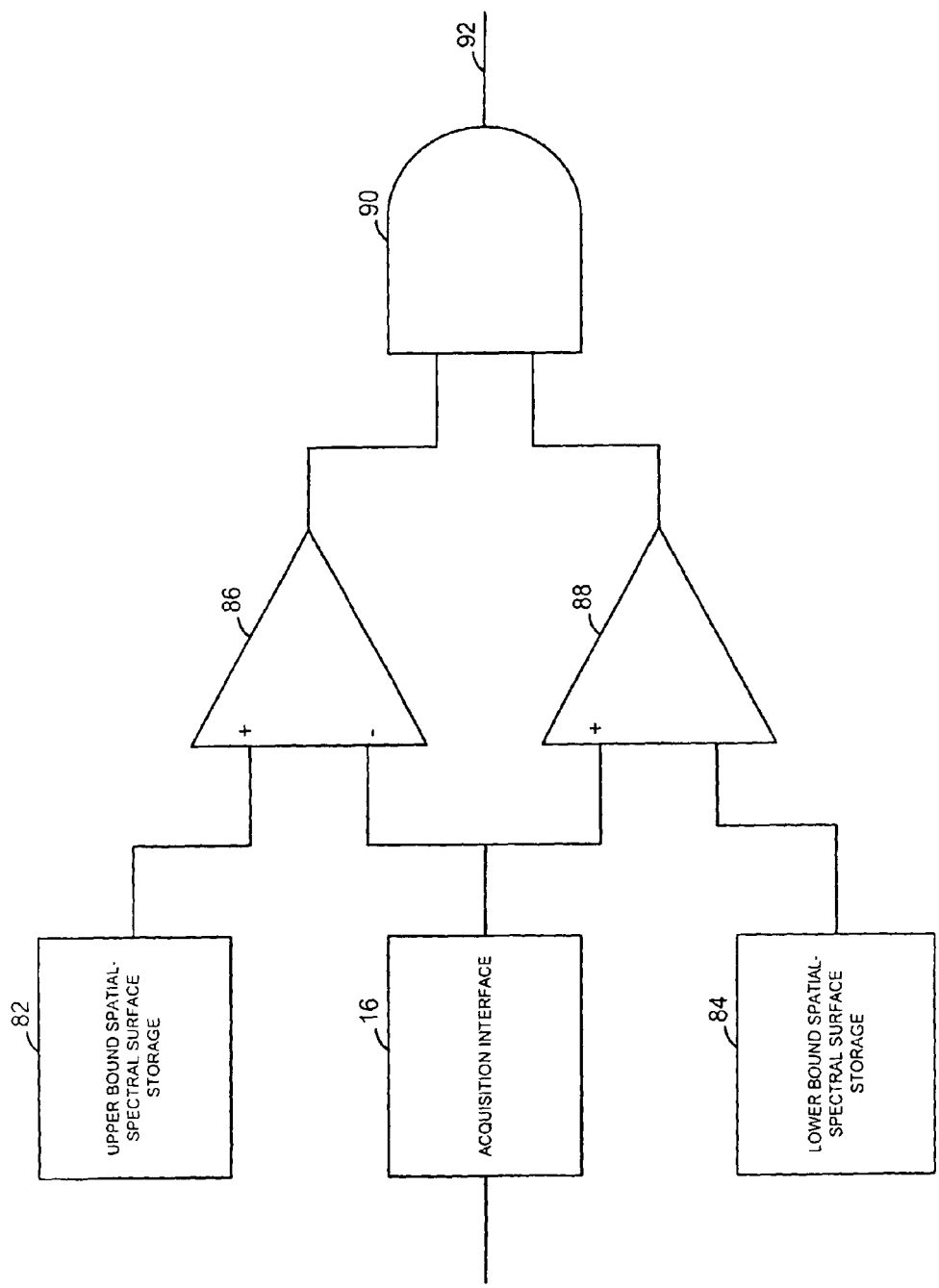
FIG. 10 is a block diagram of spectral-spatial logic that can be used in connection with the surfaces of FIG. 9.

Referring to FIGS. 9 and 10, the spectral-spatial logic that performs the comparisons can include dual-threshold comparison logic 80. This logic includes an upper bound comparator 86 responsive to upper bound spectral-spatial surface storage 82 and to the acquisition interface 16. It also includes a lower bound comparator 88 responsive to upper bound spectral-spatial surface storage 84 and to the acquisition interface 16. An output of the first comparator and an output of the second comparator are each provided to an input of an AND gate 90. This AND gate has a pass-fail output 92. The dual-threshold logic compares acquired spectral data with an upper bound spectral-spatial surface and a lower bound spectral-spatial surface. As with other components in the system, the spectral-spatial logic can be implemented in hardware, software, or both, and given the simplicity of its operations, spectral-spatial logic could readily be embedded in low-level acquisition loops or built into dedicated acquisition hardware. Data can be processed point-by-point, line-by-line, or in any other suitable manner. It may even be possible to perform spectral-spatial manipulations in the analog domain on detector signal output levels.

In operation, the dual-threshold spectral-spatial logic 80 receives acquisition data corresponding to one or more objects 74A, 74B, . . . 74Z, such as a series of pharmaceutical dosage units. The logic tests these against an upper bound surface 70 and a lower bound surface 72. Those objects whose data fall above the lower bound surface and below the upper bound surface are accepted, and those whose data fall either bellow the lower bound surface (e.g., 74N) or above the upper bound surface are rejected. Providing upper and lower bounds allows the system to test for components within a predetermined error margin with only two simple comparison operations.

Example 3

Figure 11:
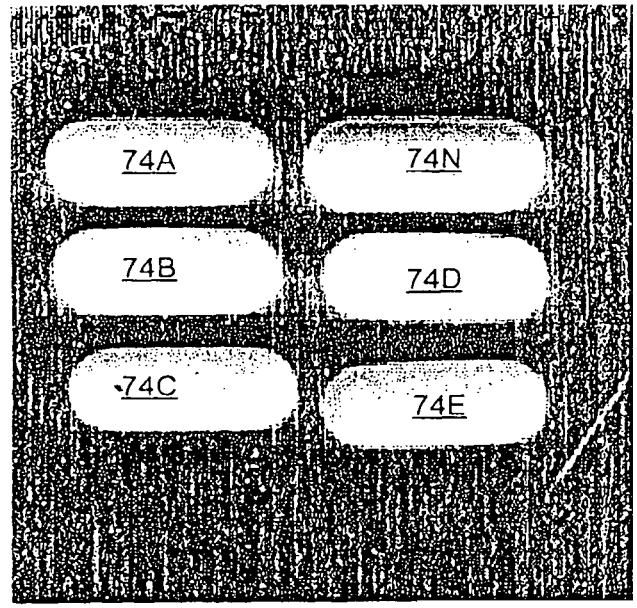
FIG. 11 is an example of an image of a series of tablets processed through the logic of FIG. 10 at a first position with respect to a variable filter.
Figure 12:
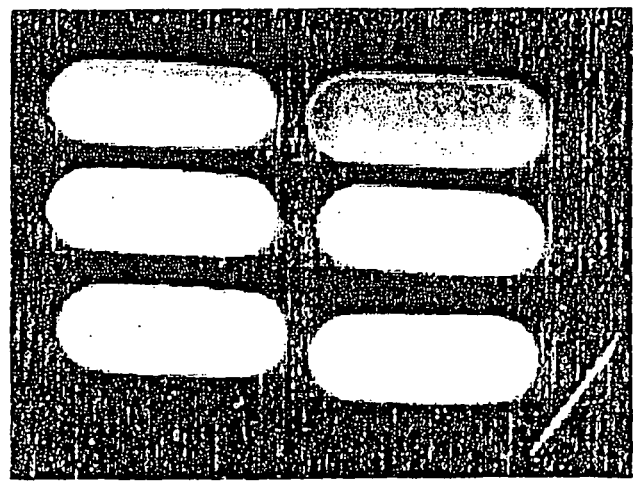
FIG. 12 is another example of an image of the same series of tablets processed through the logic of FIG. 10 at a second position with respect to a variable filter.

Referring to FIGS. 11-12, a set of six tablets was arranged in front of an array detector, with one of the tablets (suphredine hydrochloride) differing from the others (ibuprofen). An image data cube having a resolution of 320×240 pixels was acquired by moving the mixture in front of an array and variable filter with a scan range of 1050-1700 nm and a spectral resolution of 6 nm (76,800 spectra). The acquired image data were compared with two surfaces acquired for ibuprofen as images were acquired.

Images at first and second positions are shown in FIGS. 11 and 12, respectively. The image at the first position shows little differences between the tablets because their spectra are similar at the wavelength range for the portion of the filter that is in front of the different tablet. As the tablets progress along the axis of variability, however, they reach a portion of the filter where the spectral position of the different tablet falls outside of the region defined by the two planes, and the different tablet's image can be flagged.

The spectral-spatial logic can also perform other types of spectral-spatial operations. For example, it can correlate acquisition data with a single surface to determine a degree of similarity with that surface. It can also compare acquisition data with other types of spectral-spatial patterns, such as partial surfaces, lines, or volumes. And the spatial spectral logic can combine any of these operations with others, allowing for the detection of multiple chemical components and/or properties.

The stored surfaces can be derived from predictions of the chemical behavior of known substances, but they can also be simply acquired. The spectrum of a known-good sample of aspirin, for example, can be spread out to form a plane. Or a large piece of plastic that is known to be pure can be placed on a conveyor belt such that it covers the whole field of view of the detector, and an image of this piece will yield a spectral-spatial surface that can be used to test articles made of the same material and conveyed on the same belt. And if an array is divided up into several channels to monitor the same belt, the whole field of view of the array can be compared with the stored surfaces in much the same way that it would if only one channel were being monitored.

Known-good sample material can also be used as a filter between the array and sample. This type of filter generates a uniform patterned image with faint outlines, unless there is material in the sample, such as a contaminant, that is different from the filter material. As a result, the different material in the sample will stand out in the acquired image.

Using known good sample material is useful in performing pattern evolution analysis. By acquiring images of a material through a filter of the same material, only the spatial distribution of that material will be apparent in the image data. These data can therefore be evaluated or processed to derive information about the state of distribution of the material.

One important application of this technique is to monitor mixing. As two substances are mixed, an image of the outline of one of them will initially show large unmixed areas. As mixing continues, however, these areas will become smaller and smaller, making the corresponding imaged pattern finer and finer. If mixing progresses until inhomogeneities are significantly smaller than the pixel pitch, the pattern will stop changing. This progression can be monitored visually by an operator, or it can be monitored automatically using image processing techniques. Automatic monitoring can be accomplished by subtracting an image with a known-good steady-state mixed image until the difference is sufficiently small. Implementations with automatic monitoring can provide an output signal that indicates that mixing is complete, and this signal can be used as a control signal for process equipment that performs the mixing. This technique can also be used to monitor or analyze other types of patterns, such as those presented in a chromatography column.

Figure 13:
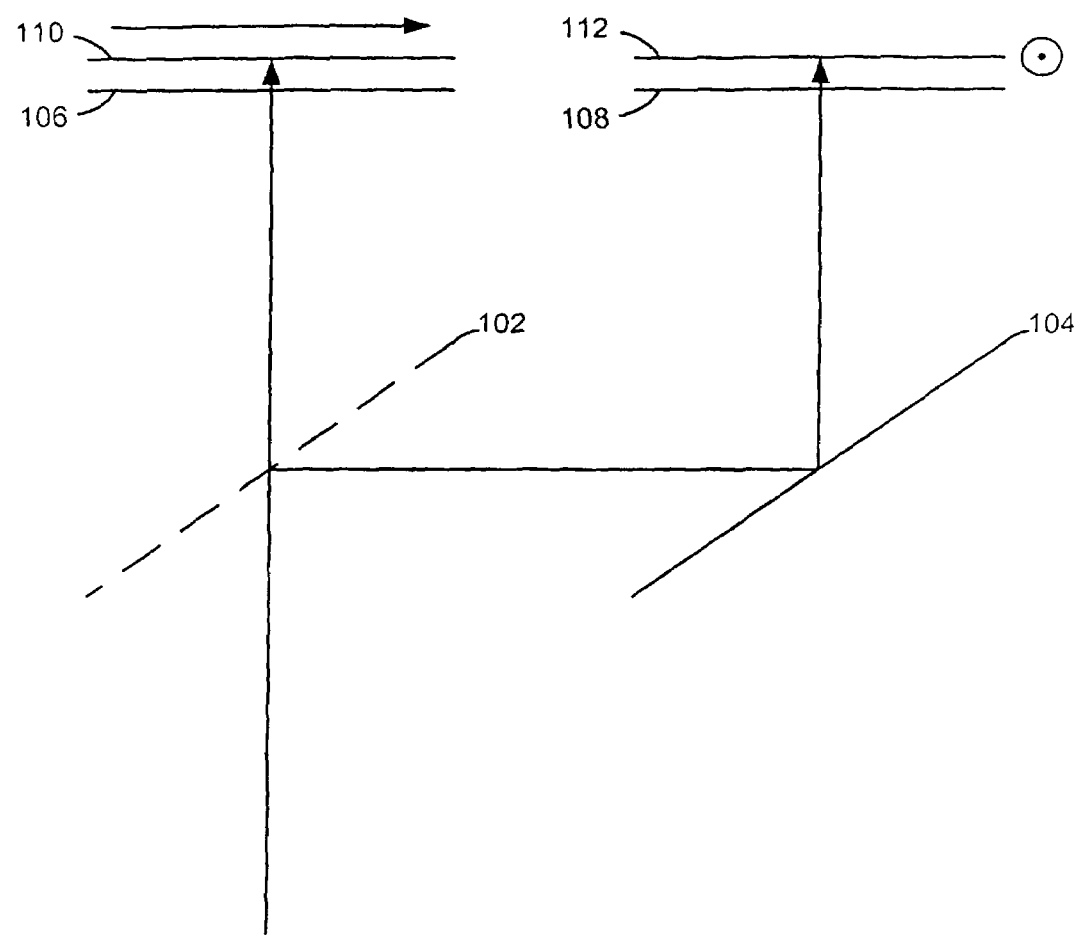
FIG. 13 is an optical schematic diagram illustrating a two-dimensional pattern evolution monitoring system with no moving parts.

It is important to observe that acquiring an image using a sample filter and then rotating some or all of the acquisition unit with respect to the sample by 90° effectively creates enough spectral information to monitor mixing progression in two dimensions. As shown in FIG. 13, a simple system can then perform these two-dimensional functions without any moving parts. Such a system can include a beam splitting mirror 102 and a second mirror 104 to direct a copy of an image sample area to two different arrays or parts of an array. The first copy is provided to the detector array or array portion through a first known-good sample material filter or filter portion 106 and then through a first variable filter or filter portion 110 having an axis of variability in one axis. The second copy is provided to the detector array or array portion through a second known-good sample material filter or filter portion 108 and then through a second variable filter or filter portion 112 having an axis of variability in a direction orthogonal to the axis of the filter or filter portion. Note that it may be possible to split the image into further copies in order to compare the image to more than one spectral-spatial surface.

Figure 14:
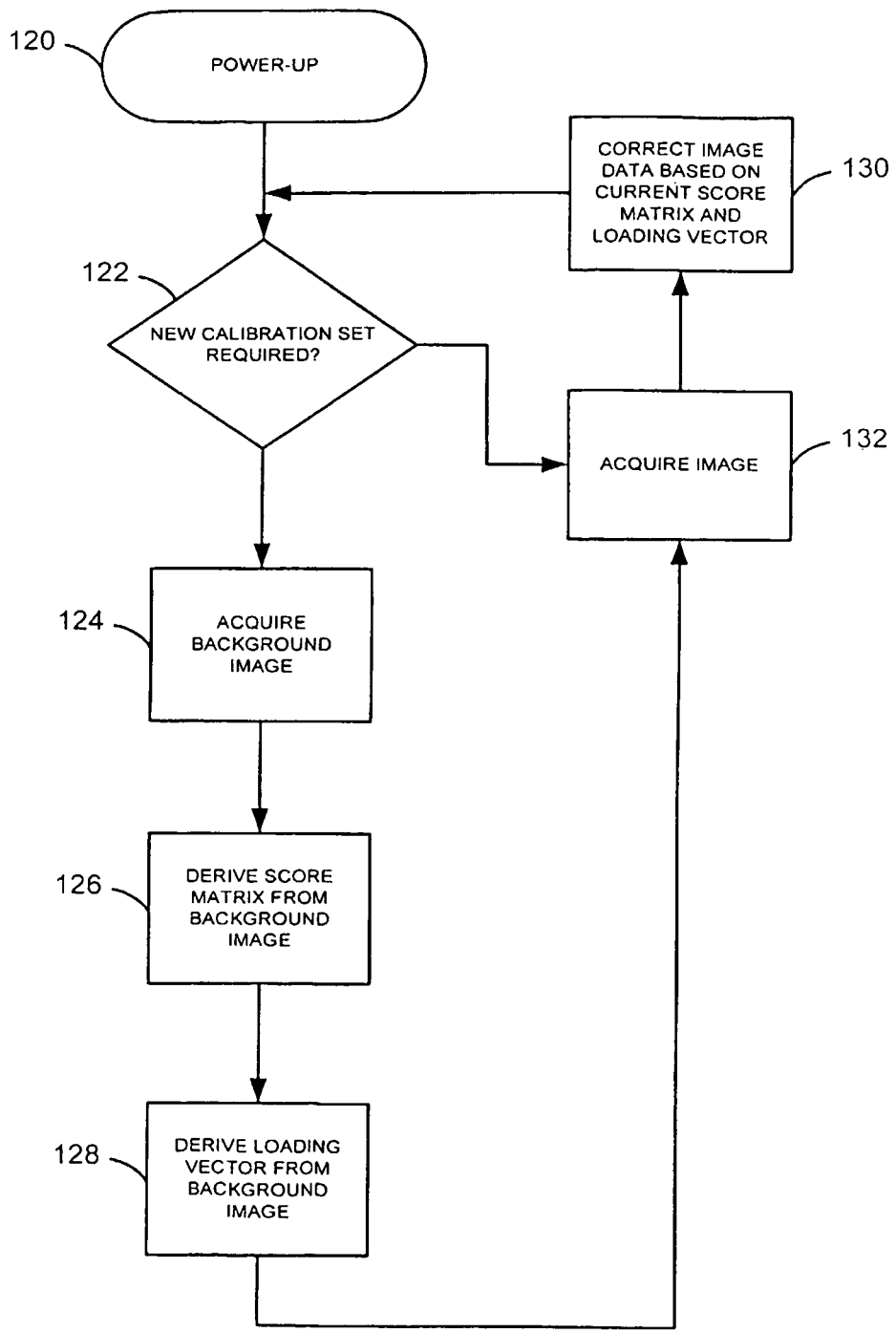
FIG. 14 is a calibration flowchart illustrating the operation of calibration logic that can be used in connection with the process control system of FIG. 1.

Referring to FIG. 14, the system 10 can also include improved calibration logic. This logic receives a background image and derives calibration information in a format that reduces noise and simplifies computations. This approach is an improvement over prior art approaches to calibration in which all values in an acquired data cube are divided by corresponding values in a calibration data cube.

The calibration logic is used to derive calibration values at power-up and/or as required (steps 120, 122). Calibration begins with the acquisition of a background image (step 124). This background image can be acquired with the system's sample area empty and the source at full intensity.

The calibration logic derives a score matrix from the background image (step 125), such as by principal component analysis. This matrix expresses background spatial intensity variability from the mean for each pixel position. The same calibration logic also derives a loading vector from the background image (step 128). This vector expresses system response as a function of wavelength. The matrices are extracted in a process known as principal component analysis.

Once the system has derived the score matrix and loading vector, it can correct acquired image data (steps 130, 132). Each value acquired is corrected for its spatial location and its wavelength using the score matrix and loading vector, respectively. Where an entire data cube is acquired, the system may correct it with a correction cube derived from the score matrix and the loading vector, rather than correcting it with the matrices themselves. Note that there may be other methods of achieving the data simplification and noise reduction inherent in this technique that flow from its fundamental principles. For example, it may be possible to use the type of information stored in the loading vector in the form of a mathematical function instead of a vector.

Figure 15:
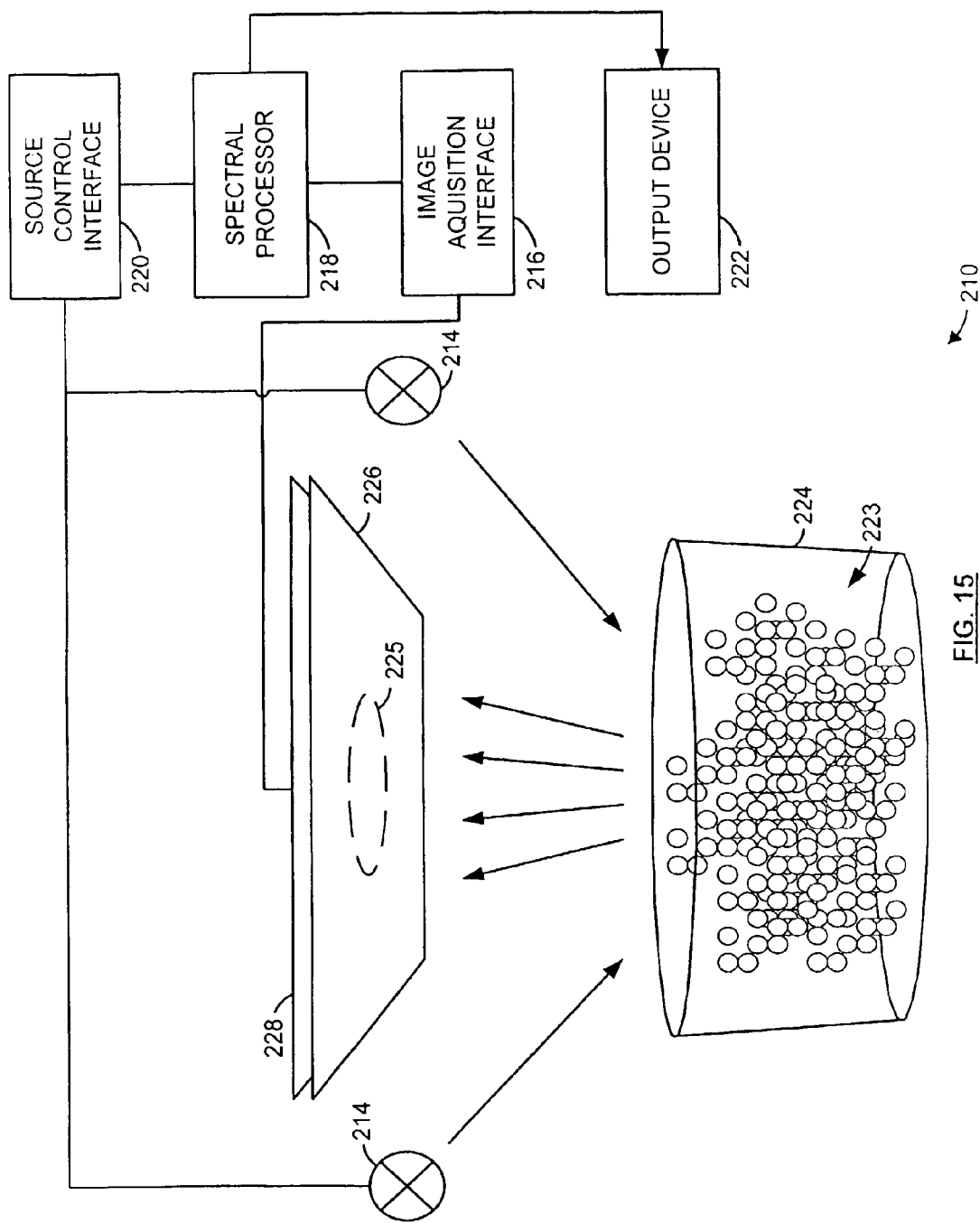
FIG. 15 is a diagram of an illustrative embodiment of another spectrometric system according to the invention, including a perspective portion illustrating its acquisition unit and a granulation or blending vessel.

Referring to FIG. 15, another type of spectrometric system 210 can be used to detect the size distribution and chemical composition of sample particles 223 in a sample vessel 224 to monitor or evaluate granulation of those particles. Because the angular distribution of scattered radiation is a sensitive measure of particle size, this type of system can be used to monitor the progress of mixing or granulation of heterogeneous mixtures, such as pharmaceuticals. It can also be used to evaluate the quality of a heterogeneous material in bulk form, or even the surface of objects such as pharmaceutical tablets.

The spectrometric system 210 can include a filter 226 and a detector array 228. An output of the array is operatively connected to an acquisition interface 216, which is in turn operatively connected to a spectral processor 218. The spectral processor has an output operatively connected to an input of an output device 222. The system can further include one or more of radiation sources 214 that can be operatively connected to a source control interface 220. The source control interface can be coupled to the spectral processor, although in some instances, separately driven or even ambient light sources might be used instead.

The filter 226 can be a simple noise-rejecting band-pass filter, a variable filter, or it may be omitted. Where it is a variable filter, it can be continuously variable filter or a blocked variable filter with as few as two areas with different filter characteristics. Although the variable filter is shown between the sample and the detector array, in other embodiments it can also be located between the sources and sample vessel.

The sources 214 are preferably narrow-band, coherent sources, such as collimated pulsed laser diodes. In one embodiment, one of the sources is resonant with the OH stretch band at 1440 nm and another is off-resonance at 1350 nm, to allow for the measurement of moisture and particle size in a continuously moving stream. In one embodiment, scattered light from the two sources is collected in alternate frames, but with a two-region filter, the light could be collected continuously, with light from one source being collected through one half of the filter and light from the other being collected through the other. Further sources and filter regions could also be provided to collect information about further spectral regions of interest. And while FIG. 15 is a conceptual presentation of a system which can be used to directly measure scattered radiation, the system can also be configured to make indirect measurements, such as by orienting the sources to shine through the sample vessel toward the array, and thereby obtaining a measurement of light that is not scattered.

In operation, the source control interface 220 causes the sources 214 to illuminate the sample particles in the sample vessel, and the acquisition interface 216 causes the detector array 228 to acquire images of a resulting scattered light pattern. In systems with variable filters, a single acquisition can provide information about the spatial distribution at two or more wavelengths. Where there is no filter or only a noise-rejection filter, the source control interface and acquisition interface can operate in synchrony to acquire a series of interleaved images for different wavelengths. Acquisition time can be varied to compensate for differences in source intensity.

The system can detect and analyze individual images, or monitor an ongoing process. A process could be monitored to determine when two ingredients were sufficiently well mixed, for example. This monitoring could be an attended process, with a technician observing information on an output device, or it could be an automated process, with the system providing a stop signal to mixing machinery.

The spectral processor 218 can analyze acquired images using well known scattering analysis techniques, such as Mie scattering analysis. Such techniques can treat the received image a series of superimposed idealized gratings. Suitable techniques are discussed, for example, in *Light Scattering by Small Particles* by H. C. van de Hulst, Dover Publications, New York, 1981.

It is also important to note that it may not be necessary to perform absolute computations based on strict mathematical models. The spectral processor can instead strive to detect an image state that has been empirically determined to correspond to desired sample properties. And where a process is monitored on an ongoing basis, it may even be sufficient to simply wait until the process has stopped changing appreciably and has therefore reached an equilibrium state.

The time resolution with which the system can detect changes in particle size would be limited ultimately by the camera frame rate. The time resolution required to avoid motion artifacts from the sample, on the other hand, is limited by the pulse duration of the laser diodes, which can be many orders of magnitude faster than the camera frame rate. Using filters and baffles, it is possible to shield the camera from light other than that from the diodes. The laser diodes will be synchronized to the camera, so that a pulse occurs at a constant phase relative to the start of integration of the camera.

Changes in the ratio of the summed scattered radiation in the two wavelength channels should be a direct measure of the moisture content of the stream. Changes in the distribution of radiation across the array will reflect changes in the particle sizes encountered by the lasers at the sample surface. Alternatively, detectors can be positioned at fixed angular positions and monitored for a discrete change in amplitude.

Figure 16:
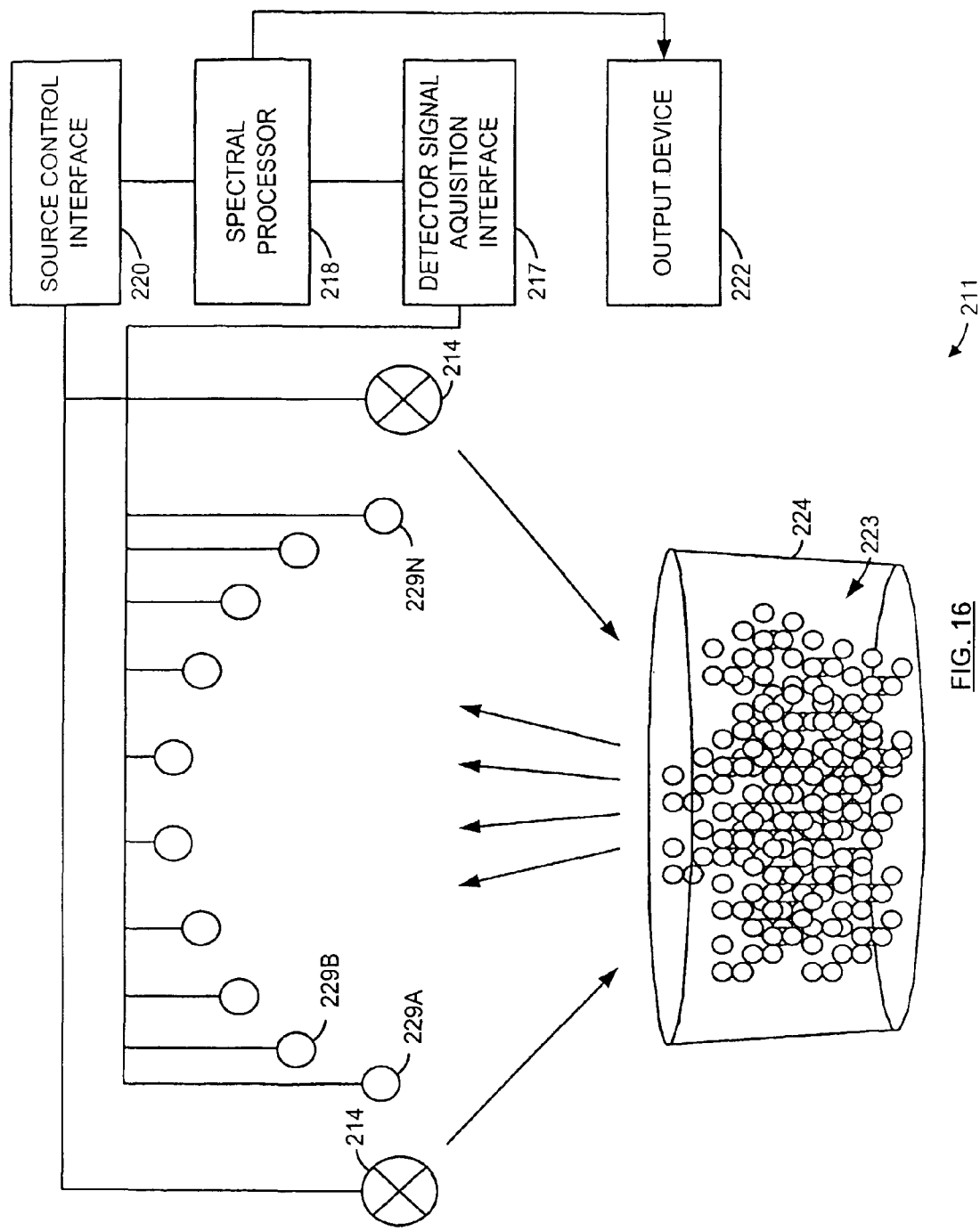
FIG. 16 is a diagram of the embodiment of FIG. 15 adapted for use with discrete detectors.

Referring to FIG. 16, the detector array can be replaced with a series of discrete detectors 229A, 229B, . . . 229N. Although a variety of different types of detectors could be used, they are preferably InGaAs sensors that have characteristics that are similar to those of the optical arrays discussed above. Because they can be monitored continuously by a detector signal acquisition interface 217, a system 211 based on them would not need to exhibit a frame-rate-based time constraint. The detectors can be positioned in a plane, a hemispherical section, or in any other suitable arrangement that allows them to receive light scattered at different angles. The number of detectors will depend on the nature of the scattering information sought, and it is contemplated that as few as 4, 8, 16, or 32 detectors could provide valuable granulation information.

The functioning of portions of the subject matter of this application is elaborated upon in two previous applications entitled "Hybrid-Scanning Spectrometer" Ser. Nos. 09/817, 785, and 09/828,281, filed on Mar. 26, 2001 and Apr. 6, 2001, respectively. The systems described in this application can also be used to examine a series of pharmaceutical dosage units, such as capsules, tablets, pellets, ampoules, or vials, or otherwise combined with the teachings described in applications entitled "High-Volume On-Line Spectroscopic Composition Testing of Manufactured Pharmaceutical Dosage Units," including application Ser. No. 09/507,293, filed on Feb. 18, 2000, application No. 60/120,859, filed on Feb. 19, 1999, and application No. 60/143,801, filed on Jul. 14, 1999 (PCT/US00/19271 and PCT/US00/19273). The concepts presented in this application can also be combined with subject matter described in applications entitled "High-Throughput Infrared Spectrometry," including application Ser. No. 09/353,325, filed Jul. 14, 1999, application No. 60/092,769 filed on Jul. 14, 1998, and application No. 60/095,800 filed on Aug. 7, 1998 (PCT/US99/15900), as well as applications entitled "Multi-Source Array," including application No. 60/183,663, filed on Feb. 18, 2000, and application Ser. No. 09/788,316, filed on Feb. 16, 2001 (PCT/US01/05262). All of the applications listed in this paragraph are herein incorporated by reference.

The present invention has now been described in connection with a number of specific embodiments thereof. However, numerous modifications which are contemplated as falling within the scope of the present invention should now be apparent to those skilled in the art. For example, a number of specific embodiments can be tailored to obtain transmission or reflectance image data for a variety of types of samples depending on the data required from the system in particular circumstances. And features of the various embodiments described can be used separately or combined in various ways to achieve particular goals. For example, while direct coupling of the array, filter, and vessel coupled with a spectral-spatial analysis module can provide for a highly versatile system, these two features can each also be employed alone or in combination with other features. It should also be emphasized that some of the features of the system described are independent of the type of acquisition hardware. For example, the statistical mixing analysis, the trace analysis, and improved calibration can be used with any suitable spectral imaging instrument, such as a detector array cascaded with an LCTF. It is therefore intended that the scope of the present invention be limited only by the scope of the claims appended hereto. In addition, the order of presentation of the claims should not be construed to limit the scope of any particular term in the claims.

What is claimed is:

1. A spectrometric apparatus, comprising:
   an array of detector elements that are at least generally aligned in at least a first direction, and that are responsive to incident radiation to produce an output signal that includes information from the incident radiation,
   a variable filter having spectral characteristics that vary along at least along the first direction,
   at least one vessel having a volume disposed in a field of view of the array of detector elements through the variable filter, and
   an indirect driver operative to move contents of the vessel through the field of view of the array, wherein the driver is a heat source.

2. The apparatus of claim 1 wherein the indirect driver is a passive driver.

3. The apparatus of claim 1 wherein the indirect driver is incidental to a process being monitored by the array.

4. The apparatus of claim 1 wherein the array is an array of infrared detector elements that are responsive to incident infrared radiation to produce the output signal.

5. The apparatus of claim 1 wherein the array is an array of ultraviolet detector elements that are responsive to incident ultraviolet radiation to produce the output signal.

6. The apparatus of claim 1 wherein the array is an array of visible-range detector elements that are responsive to incident visible light to produce the output signal.

7. The apparatus of claim 1 further including a narrow-band source and wherein the detector array and the variable filter are operative on wavelengths outside of the bandwidth of the source.

8. The apparatus of claim 1 wherein the detector array is a two-dimensional detector array.

9. The apparatus of claim 1 wherein the variable filter is a variable band-pass filter.

10. The apparatus of claim 1 wherein the variable filter is a continuously variable filter.

11. The apparatus of claim 1 further including multivariate spectral analysis logic responsive to the output signal.

12. A spectrometric apparatus, comprising:
    a detector that is responsive to incident radiation from different areas in a chemically heterogeneous sample illuminated by a radiation source to produce an output signal that includes information about the different areas from the incident radiation,
    a spectrally selective element in an optical path between the radiation source and the detector to provide spectral information in the output signal about the different areas in the field of view,
    a spectral processor operative to derive chemical data sets from the different areas in the sample wherein the chemical data sets include spectral information about the areas having different chemical properties, and
    an analysis module operative to statistically analyze the spectral information for the different areas in the derived chemical data sets to provide a statistical measure of uniformity of distribution of chemical properties.

13. The apparatus of claim 12 wherein the detector is an array detector and wherein the analysis module is operative to compute a mean value of spectral information received by the different detectors in the array.

14. The apparatus of claim 13 wherein the analysis module is operative to compute a mean concentration from the distribution.

15. The apparatus of claim 12 wherein the analysis module is operative to compute a skew value for the distribution of spectral information received by the detector.

16. The apparatus of claim 12 wherein the analysis module is operative to compute a standard deviation for the distribution of spectral information received by the detector.

17. The apparatus of claim 12 wherein the analysis module is operative to compute a kurtosis value for the distribution of spectral information received by the detector.

18. The apparatus of claim 12 wherein the analysis module is operative to analyze a distribution of chemical species concentration.

19. The apparatus of claim 12 wherein the analysis module is operative to analyze a distribution of a plurality of chemical species concentrations.

20. The apparatus of claim 19 wherein the analysis module is operative to analyze the distribution by calculating concentrations for the plurality of species at each area and then combining results of these distribution calculations.

21. The apparatus of claim 12 wherein the detector is an infrared detector responsive to incident infrared radiation to produce the output signal.

22. The apparatus of claim 12 wherein the detector is a near-infrared detector responsive to incident near-infrared radiation to produce the output signal.

23. The apparatus of claim 12 wherein the detector is an ultraviolet detector responsive to incident ultraviolet radiation to produce the output signal.

24. The apparatus of claim 12 wherein the detector is a visible-range detector responsive to incident visible light to produce the output signal.

25. The apparatus of claim 12 wherein the source is a narrow-band source and wherein the detector and the spectrally sensitive element are operative on wavelengths outside of the bandwidth of radiation from the source.

26. The apparatus of claim 12 wherein the detector is a two-dimensional detector array.

27. The apparatus of claim 12 wherein the analysis module includes multivariate spectral analysis logic responsive to the output signal.

28. The apparatus of claim 12 wherein the analysis module includes component analysis logic.

29. The apparatus of claim 12 further including a display module responsive to the analysis module and operative to provide a display signal that expresses results from the analysis module.

30. The apparatus of claim 12 further including a threshold module responsive to the analysis module and operative to provide an accept/reject signal that expresses results from the analysis module.

31. The apparatus of claim 12 wherein the analysis module is operative to compute both an overall amount value and distribution of amount information from the output signal of the detector.

32. The apparatus of claim 12 wherein the detector is an array detector including a plurality of detector elements and further including a plurality of radiation channels optically coupled, to at least a subset of detector elements in the array detector.

33. The apparatus of claim 32 wherein the radiation channels direct the radiation through the spectrally selective element.

34. The apparatus of claim 32 wherein the radiation channels are optical fibers.

35. The apparatus of claim 32 wherein the channels collect infrared radiation.

36. The apparatus of claim 32 wherein the channels collect ultraviolet radiation.

37. The apparatus of claim 32 wherein the channels collect visible radiation.

38. The apparatus of claim 32 wherein the channels collect wavelengths outside of a bandwidth of the source radiation.

39. The apparatus of claim 12 wherein the spatially selective detector is a two-dimensional image detector made up of a two-dimensional array of detector elements, wherein the spectrally selective element is a variable filter deposited on the surface of the array and having spectral characteristics that vary along at least one dimension of the array, and wherein the spectral processor is operative to derive spatially mixed data sets.

40. The apparatus of claim 12 further including a spreading element operative to spread the sample over a field of field of view of the apparatus.

41. An apparatus for detecting properties of a heterogeneous sample, comprising:
   a two-dimensional array of detector elements that are at least generally aligned in at least a first direction and a second direction, and that are responsive to incident radiation to produce an output signal that includes spatial information from the incident radiation,
   a sample vessel mounted to the array and defining a sample volume for a heterogeneous sample,
   wherein the detector elements of the array are each responsive to a corresponding portion of a sample in the sample volume along substantially parallel optical paths, and
   a display responsive to the spatial information in the output signal to display a spatial image of the heterogeneous sample.

42. The apparatus of claim 41 further including a filter between the array and the vessel.

43. The apparatus of claim 42 wherein the vessel is coupled to the array without any intermediate optical elements except the filter.

44. The apparatus of claim 42 wherein the filter includes known good sample material.

45. The apparatus of claim 42 wherein the filter is a variable band-pass filter.

46. The apparatus of claim 42 wherein the filter is a continuously variable filter.

47. The apparatus of claim 42 further including a narrow-band source and wherein the detector array and the variable filter are operative on wavelengths outside of the bandwidth of the source.

48. The apparatus of claim 42 wherein the array is a semiconductor array and the filter is deposited directly on the semiconductor array itself.

49. The apparatus of claim 42 wherein the variable filter is deposited on an intermediate layer in the sandwiched structure.

50. The apparatus of claim 41 wherein the vessel forms part of an open process conduit.

51. The apparatus of claim 41 wherein the detector array is an integrated semiconductor detector array.

52. The apparatus of claim 41 wherein the array is an array of infrared detector elements that are responsive to incident infrared radiation to produce the output signal.

53. The apparatus of claim 41 wherein the array is an array of ultraviolet detector elements that are responsive to incident ultraviolet radiation to produce the output signal.

54. The apparatus of claim 41 wherein the array is an array of visible-range detector elements that are responsive to incident visible light to produce the output signal.

55. The apparatus of claim 41 further including multivariate spectral analysis logic responsive to the output signal.

56. The apparatus of claim 41 further including an indirect driver operative to move the sample relative to the array.

57. The apparatus of claim 56 wherein the indirect driver is a passive driver.

58. The apparatus of claim 56 wherein the indirect driver is incidental to a process being monitored by the array.

59. The apparatus of claim 56 wherein the indirect driver is a gravity-driven flow channel.

60. The apparatus of claim 56 wherein the driver is a restricted gravity-driven flow channel.

61. The apparatus of claim 56 wherein the driver operates by one of the following mechanisms: elution, sedimentation, capillary action, viscous friction, evaporation, convection, and gravity.

62. The apparatus of claim 56 wherein the driver is a heat source.

63. The apparatus of claim 56 wherein the driver is a mixing element.

64. The apparatus of claim 56 further including an externally applied gradient driver applied perpendicularly to an axis of progression of the indirect driver.

65. An apparatus for detecting properties of a heterogeneous sample, comprising:
   a sandwiched structure including:
      a) a two-dimensional array of detector elements that are at least generally aligned in at least a first direction and a second direction, and that are responsive to incident radiation to produce an output signal that includes spatial information from the incident radiation,
      b) a wall mounted to the array between the array and a sample volume for a heterogeneous sample, and
      c) wherein the detector elements of the array are each responsive to a corresponding portion of a sample in the sample volume along substantially parallel optical paths, and
   a display responsive to the spatial information in the output signal to display a spatial image of the heterogeneous sample.

66. The apparatus of claim 65 further including a filter between the array and the wall.

67. The apparatus of claim 66 wherein the wall is coupled to the array without any intermediate optical elements except the filter.

68. The apparatus of claim 66 wherein the filter includes known good sample material.

69. The apparatus of claim 66 wherein the filter is a variable band-pass filter.

70. The apparatus of claim 66 wherein the filter is a continuously variable filter.

71. The apparatus of claim 66 further including a narrow-band source and wherein the detector array and the variable filter are operative on wavelengths outside of the bandwidth of the source.

72. The apparatus of claim 66 wherein the array is a semiconductor array and the filter is deposited directly on the semiconductor array itself.

73. The apparatus of claim 66 wherein the variable filter is deposited on an intermediate layer in the sandwiched structure.

74. The apparatus of claim 65 wherein the wall forms part of an open process conduit.

75. The apparatus of claim 65 wherein the detector array is an integrated semiconductor detector array.

76. The apparatus of claim 65 wherein the array is an array of infrared detector elements that are responsive to incident infrared radiation to produce the output signal.

77. The apparatus of claim 65 wherein the array is an array of ultraviolet detector elements that are responsive to incident ultraviolet radiation to produce the output signal.

78. The apparatus of claim 65 wherein the array is an array of visible-range detector elements that are responsive to incident visible light to produce the output signal.

79. The apparatus of claim 65 further including multivariate spectral analysis logic responsive to the output signal.

80. The apparatus of claim 65 further including an indirect driver operative to move the sample relative to the array.

81. The apparatus of claim 80 wherein the indirect driver is a passive driver.

82. The apparatus of claim 80 wherein the indirect driver is incidental to a process being monitored by the array.

83. The apparatus of claim 80 wherein the indirect driver is a gravity-driven flow channel.

84. The apparatus of claim 80 wherein the driver is a restricted gravity-driven flow channel.

85. The apparatus of claim 80 wherein the driver operates by one of the following mechanisms: elution, sedimentation, capillary action, viscous friction, evaporation, convection, and gravity.

86. The apparatus of claim 80 wherein the driver is a heat source.

87. The apparatus of claim 80 wherein the driver is a mixing element.

88. The apparatus of claim 80 further including an externally applied gradient driver applied perpendicularly to an axis of progression of the indirect driver.

89. An apparatus for detecting properties of a heterogeneous sample, comprising:
   a two-dimensional array of detector elements that are at least generally aligned in at least a first direction and a second direction, and that are responsive to incident radiation to produce an output signal that includes spatial information from the incident radiation,
   a sample vessel mounted to the array and defining a sample volume for a heterogeneous sample,
   wherein the detector elements of the array are each responsive to a corresponding portion of a sample in the sample volume along substantially parallel optical paths, and
   spatial information storage responsive to the spatial information in the output signal to store a spatial image of the heterogeneous sample.

90. An apparatus for detecting properties of a heterogeneous sample, comprising:
   a sandwiched structure including:
   a) a two-dimensional array of detector elements that are at least generally aligned in at least a first direction and a second direction, and that are responsive to incident radiation to produce an output signal that includes spatial information from the incident radiation,
   b) a wall mounted to the array between the array and a sample volume for a heterogeneous sample, and
   c) wherein the detector elements of the array are each responsive to a corresponding portion of a sample in the sample volume along substantially parallel optical paths, and
   spatial information storage responsive to the spatial information in the output signal to store a spatial image of the heterogeneous sample.

91. The apparatus of claim 90 wherein the wall forms part of a capillary.

92. The apparatus of claim 41 wherein the vessel is a capillary.

93. The apparatus of claim 65 wherein the wall forms part of a capillary.

94. The apparatus of claim 89 wherein the vessel is a capillary.

* * * * *